US011515031B2

United States Patent
Takaya et al.

(10) Patent No.: US 11,515,031 B2
(45) Date of Patent: Nov. 29, 2022

(54) IMAGE PROCESSING APPARATUS, X-RAY DIAGNOSTIC APPARATUS, AND IMAGE PROCESSING METHOD

(71) Applicant: CANON MEDICAL SYSTEMS CORPORATION, Otawara (JP)

(72) Inventors: Mika Takaya, Otawara (JP); Ryoichi Nagae, Nasushiobara (JP); Sho Sasaki, Utsunomiya (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 11 days.

(21) Appl. No.: 16/385,567

(22) Filed: Apr. 16, 2019

(65) Prior Publication Data

US 2019/0318823 A1    Oct. 17, 2019

(30) Foreign Application Priority Data

Apr. 16, 2018 (JP) .............................. JP2018-078592
Apr. 16, 2019 (JP) .............................. JP2019-077504

(51) Int. Cl.
  *A61F 2/07*   (2013.01)
  *G16H 30/40*  (2018.01)
  *G06T 7/00*   (2017.01)
  *A61B 34/20*  (2016.01)
  *A61B 6/00*   (2006.01)
  *A61B 34/10*  (2016.01)

(52) U.S. Cl.
  CPC ........... *G16H 30/40* (2018.01); *A61B 6/5205* (2013.01); *A61B 34/20* (2016.02); *G06T 7/0012* (2013.01); *A61B 2034/107* (2016.02); *G06T 2207/10116* (2013.01)

(58) Field of Classification Search
  CPC ....................................................... A61F 2/07
  See application file for complete search history.

(56) References Cited

U.S. PATENT DOCUMENTS

| 6,307,914 | B1* | 10/2001 | Kunieda | A61B 6/12 378/65 |
|---|---|---|---|---|
| 10,702,226 | B2* | 7/2020 | Barak | A61B 6/12 |
| 2009/0281418 | A1* | 11/2009 | Ruijters | A61B 6/481 600/424 |
| 2010/0099979 | A1* | 4/2010 | Schoonenberg | G06T 7/0012 600/424 |

(Continued)

FOREIGN PATENT DOCUMENTS

| JP | 2007-185278 | 7/2007 |
|---|---|---|
| JP | 2009-018184 | 1/2009 |

(Continued)

*Primary Examiner* — Cindy Trandai
(74) *Attorney, Agent, or Firm* — Oblon, McClelland, Maier & Neustadt, L.L.P.

(57) ABSTRACT

A medical image-processing apparatus according to an embodiment includes processing circuitry configured to determine a position of a feature point of a device in a first X-ray image, and generate a superimposed image in which a 3D model expressing the device is superimposed on the first X-ray image or a second X-ray image that is acquired later than the first X-ray image. The processing circuitry is configured to superimpose the 3D model on the first X-ray image or the second X-ray image at a position based on the position of the feature point.

19 Claims, 10 Drawing Sheets

(56) References Cited

U.S. PATENT DOCUMENTS

| | | | |
|---|---|---|---|
| 2011/0160833 A1* | 6/2011 | Gonzalez | A61F 2/95 623/1.11 |
| 2012/0250964 A1* | 10/2012 | Pfister | A61B 6/504 382/130 |
| 2012/0250973 A1* | 10/2012 | Nambu | A61B 6/12 382/132 |
| 2012/0277570 A1* | 11/2012 | Todor | A61N 5/103 600/407 |
| 2013/0010924 A1* | 1/2013 | Ohishi | A61B 6/487 378/42 |
| 2013/0137974 A1* | 5/2013 | Sakaguchi | A61B 6/503 600/424 |
| 2014/0031676 A1 | 1/2014 | Nempont et al. | |
| 2014/0094693 A1* | 4/2014 | Cohen | G06T 7/33 600/424 |
| 2014/0183374 A1* | 7/2014 | Sakaguchi | A61B 6/54 250/394 |
| 2015/0073535 A1* | 3/2015 | Consigny | A61L 31/10 623/1.38 |
| 2017/0085855 A1* | 3/2017 | Roberts | A61B 5/0042 |
| 2018/0008352 A1* | 1/2018 | Flexman | A61B 34/20 |
| 2018/0021000 A1* | 1/2018 | Akiyama | A61B 6/481 378/62 |
| 2018/0218508 A1* | 8/2018 | Lee | G06T 7/174 |
| 2019/0000318 A1* | 1/2019 | Caluser | A61B 5/0073 |
| 2019/0038111 A1* | 2/2019 | Endo | A61B 1/00009 |
| 2019/0059841 A1* | 2/2019 | Palma | G06T 5/003 |
| 2019/0227325 A1* | 7/2019 | Tomizawa | G06T 19/006 |
| 2019/0231198 A1* | 8/2019 | Hirota | A61B 8/13 |
| 2021/0077047 A1* | 3/2021 | Tolkowsky | A61B 90/39 |

FOREIGN PATENT DOCUMENTS

| | | |
|---|---|---|
| JP | 2013-056113 | 3/2013 |
| JP | 2014-514082 | 6/2014 |
| JP | 2017-086413 | 5/2017 |
| WO | WO 02/064011 A2 | 8/2002 |
| WO | WO 2005/011499 A1 | 2/2005 |
| WO | WO 2012/140553 A1 | 10/2012 |

* cited by examiner

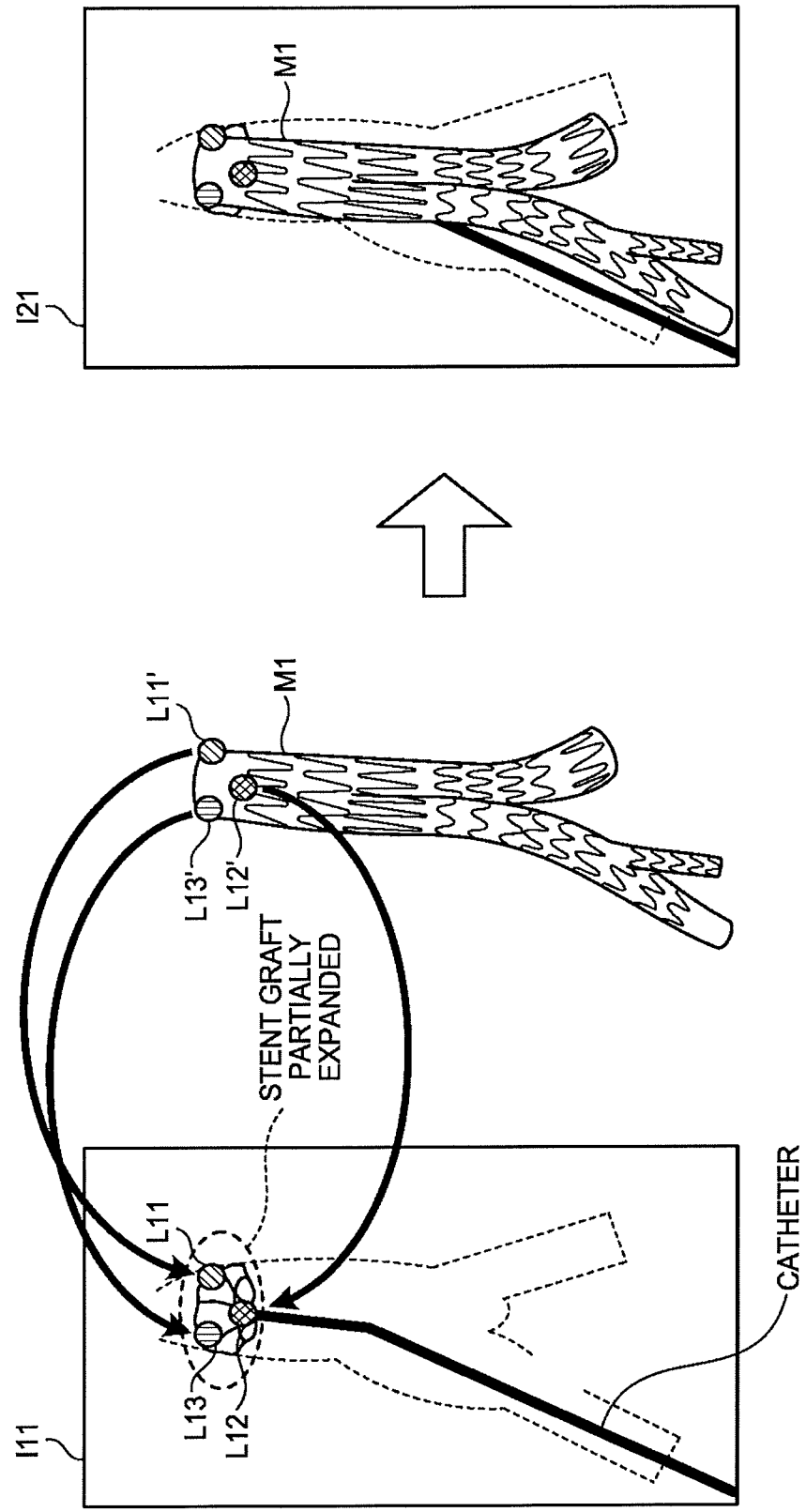

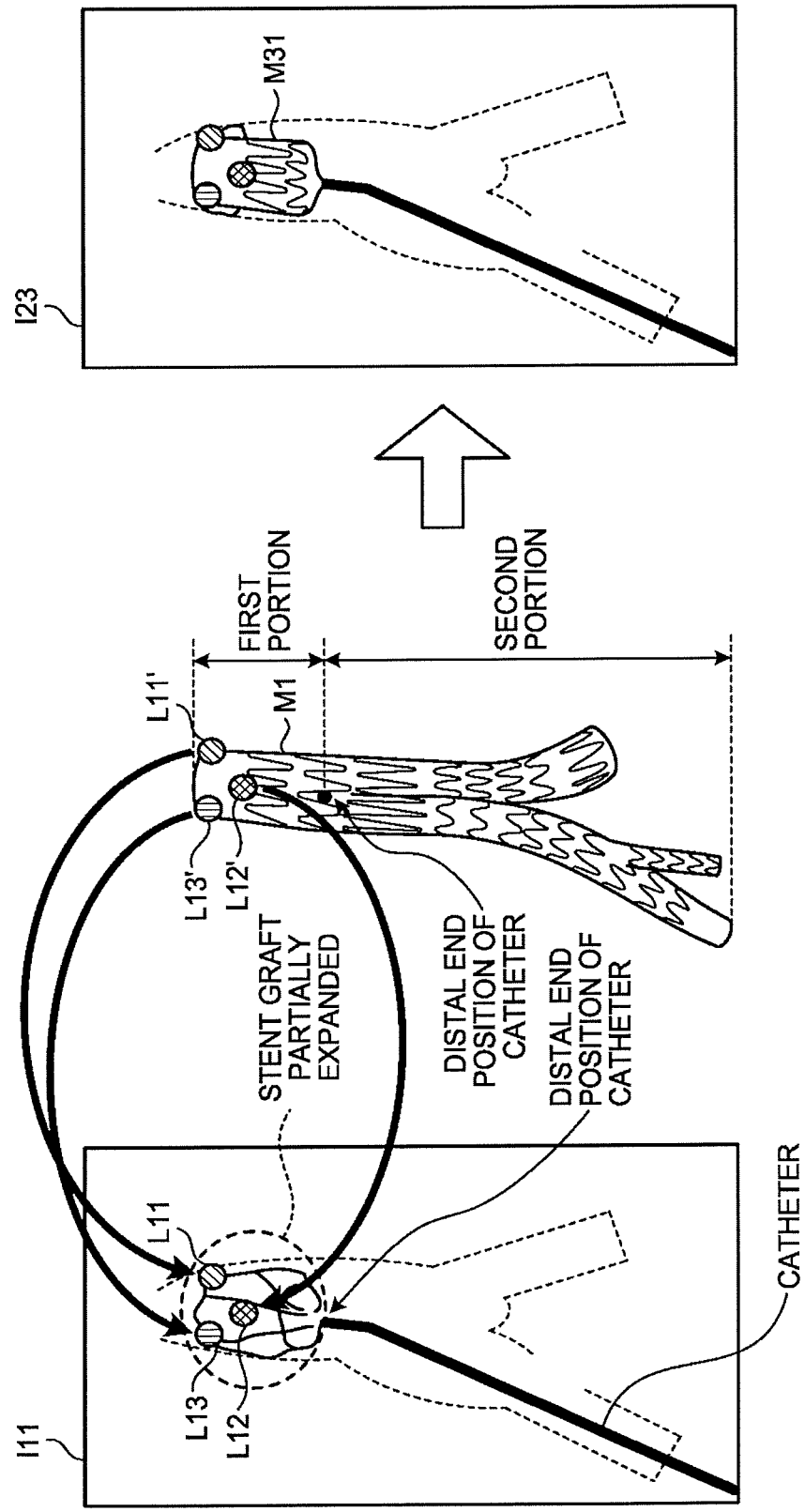

IMAGE PROCESSING APPARATUS, X-RAY DIAGNOSTIC APPARATUS, AND IMAGE PROCESSING METHOD

CROSS-REFERENCE TO RELATED APPLICATIONS

This application is based upon and claims the benefit of priority from Japanese Patent Application No. 2018-78592, filed on Apr. 16, 2018; and Japanese Patent Application No. 2019-77504, filed on Apr. 16, 2019, the entire contents of all of which are incorporated herein by reference.

FIELD

Embodiments described herein relate generally to an image processing apparatus, an X-ray diagnostic apparatus, and an image processing method.

BACKGROUND

In recent years, various kinds of medical treatment have been known in which a device is inserted and operated in a body of a subject, and the device is indwelled in the body of the subject. For example, in stent graft indwelling, an operator, such as a doctor, manufactures a stent graft according to a shape of an artery of a subject, and plans an indwelling position of the stent graft. The operator then inserts the stent graft in the body of the subject, and indwells the stent graft according to the preoperative plan.

BRIEF DESCRIPTION OF THE DRAWINGS

FIG. 5 is a diagram for describing generation of a superimposed image according to the first embodiment;

FIG. 6 is a diagram for describing generation of a superimposed image according to the first embodiment;

DETAILED DESCRIPTION

A medical image-processing apparatus according to embodiments includes processing circuitry configured to determine a position of a feature point of a device in a first X-ray image, and generate a superimposed image in which a three-dimensional (3D) model expressing the device is superimposed on the first X-ray image or a second X-ray image that is acquired at a later time than the first X-ray image. The processing circuitry is configured to superimpose the 3D model on the first X-ray image or the second X-ray image, at a position based on the determined position of the feature point.

Hereinafter, embodiments of an image processing apparatus, an X-ray diagnostic apparatus, and an image processing method are described in detail with reference to the drawings.

First, a first embodiment is described. In the first embodiment, a medical image-processing system that includes the image processing apparatus is described by way of example. Moreover, in the first embodiment, a stent graft is described as an example of the device.

Figure 1:
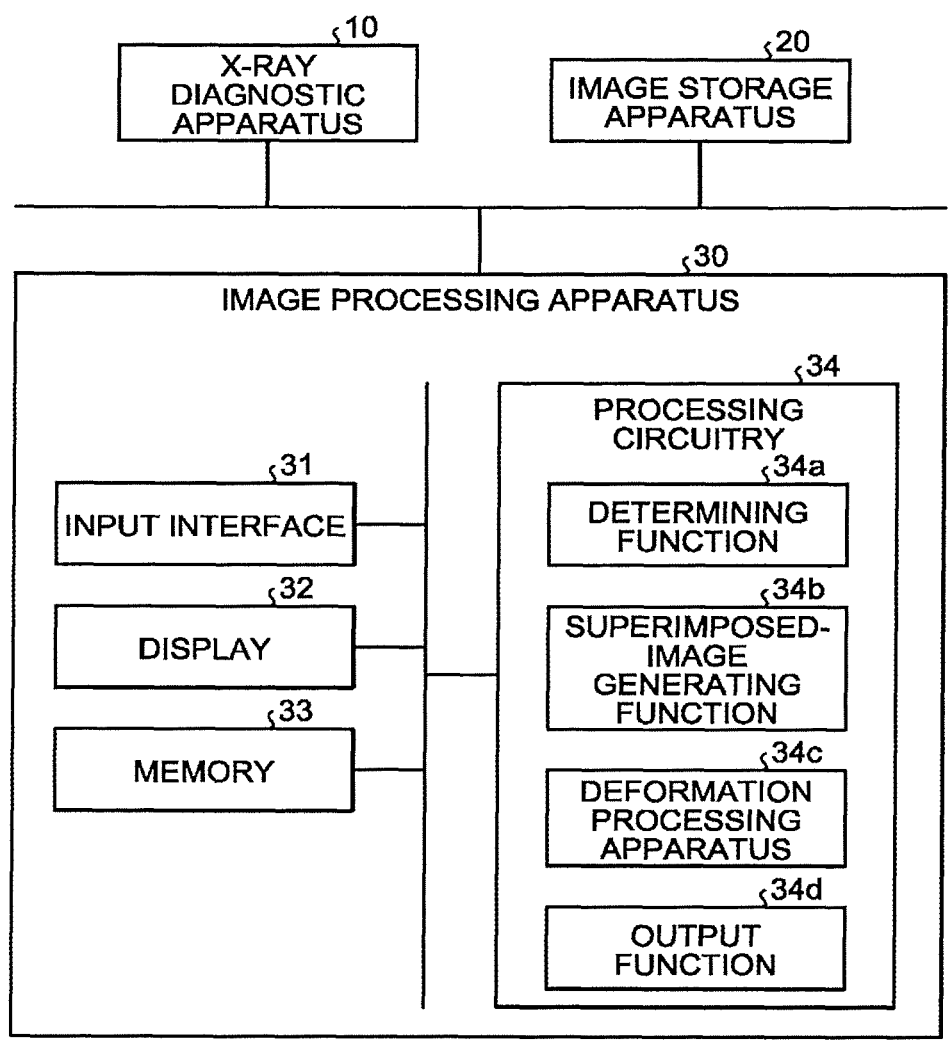
FIG. 1 is a block diagram illustrating an example of a configuration of a medical image-processing system according to a first embodiment.

As illustrated in FIG. 1, a medical image-processing system 1 according to the first embodiment includes an X-ray diagnostic apparatus 10, an image storage apparatus 20, and an image processing apparatus 30. FIG. 1 is a block diagram illustrating an example of a configuration of the medical image-processing system according to the first embodiment. As illustrated in FIG. 1, the X-ray diagnostic apparatus 10, the image storage apparatus 20, and the image processing apparatus 30 are mutually connected through a network.

The X-ray diagnostic apparatus 10 is an apparatus that acquires an X-ray image from a subject P. The X-ray image processed as data is also described as X-ray image data. For example, the X-ray diagnostic apparatus 10 acquires an X-ray image data from the subject P to which a stent graft is inserted, and transmits the acquired X-ray image data to the image storage apparatus 20 and the image processing apparatus 30. A configuration of the X-ray diagnostic apparatus 10 is described later.

The image storage apparatus 20 is an apparatus that stores an X-ray image data acquired by the X-ray diagnostic apparatus 10. For example, the image storage apparatus 20 acquires an X-ray image data from the X-ray diagnostic apparatus 10 through a network, and stores the acquire X-ray image data in a memory provided in the apparatus or outside the apparatus. For example, the image storage apparatus 20 is implemented by a computer device, such as a server device.

The image processing apparatus 30 acquires X-ray image data through a network, and performs various kinds of processing using the acquired X-ray image data. For example, the image processing apparatus 30 acquires X-ray image data from the image storage apparatus 20. Alternatively, the image processing apparatus 30 acquires X-ray image data directly from the X-ray diagnostic apparatus 10, bypassing the image storage apparatus 20. Moreover, the image processing apparatus 30 determines a position of a feature point of the stent graft in the acquired X-ray image data. Furthermore, the image processing apparatus 30 generates a superimposed image in which a 3D model expressing the stent graft on the X-ray image data based on the determined position of the feature point. The processing performed by the image processing apparatus 30 is described in detail later. For example, the image processing apparatus 30 is implemented by a computer device, such as a workstation.

Note that the X-ray diagnostic apparatus 10, the image storage apparatus 20, and the image processing apparatus 30 may be installed at any sites as long as being connectable to one another through a network. For example, the image processing apparatus 30 may be installed in a hospital different from that of the X-ray diagnostic apparatus 10. Moreover, FIG. 1 illustrates a single unit of the X-ray diagnostic apparatus 10, but the medical image-processing system 1 may include multiple units of the X-ray diagnostic apparatus.

As illustrated in FIG. 1, the image processing apparatus 30 includes an input interface 31, a display 32, a memory 33, and processing circuitry 34.

The input interface 31 receives various kinds of input operation from an operator, converts the accepted input operation into an electrical signal, and output the signal to the processing circuitry 34. For example, the input interface 31 is implemented by a mouse, a keyboard, a trackball, a switch, a button, a joystick, a touch pad that enables to make an input operation by a touch to an operating surface, a touch screen constituted of a display screen and a touch pad integrated, a non-contact input circuit that uses an optical sensor, a voice input circuit, or the like. The input interface 31 may be constituted of a tablet terminal or the like that is capable of wireless communication with the main unit of the image processing apparatus 30. Furthermore, the input interface 31 is not limited to one that includes a physical operation part, such as a mouse and a keyboard. For example, an electrical-signal processing circuit that receives an electrical signal corresponding to an input operation from an external input device provided separately from the image processing apparatus 30, and that outputs this electrical signal to the processing circuitry 34 is also included in examples of the input interface 31.

The display 32 displays various kinds of information. For example, the display 32 displays, under control of the processing circuitry 34, an X-ray image acquired by the X-ray diagnostic apparatus 10, or a superimposed image generated by the processing circuitry 34. Moreover, the display 32 displays a graphical user interface (GUI) to receive various kinds of instructions, various kinds of settings, and the like from the operator through the input interface 31. For example, the display 32 is a liquid crystal display or a cathode ray tube (CRT) display. The display 32 may be of a desktop type, or be constituted of a tablet terminal capable of wireless communication with the main unit of the image processing apparatus 30.

The memory 33 is implemented by, for example, a semiconductor memory device, such as a random access memory (RAM) and a flash memory, a hard disk, an optical disk, or the like. For example, the memory 33 stores X-ray image data acquired from the X-ray diagnostic apparatus 10 or the image storage apparatus 20. Moreover, for example, the memory 33 stores a superimposed image that is generated by the processing circuitry 34. Furthermore, for example, the memory 33 stores a program for circuitry included in the image processing apparatus 30 to implement its function. Note that the memory 33 may be implemented by a server group (cloud) that is connected with the image processing apparatus 30 through a network.

The processing circuitry 34 controls the overall operation of the image processing apparatus 30 by performing a determining function 34a, a superimposed-image generating function 34b, a deformation processing function 34c, and an output function 34d. The determining function 34a is part of a determining unit. The superimposed-image generating function 34b is part of a superimposed-image generating unit. Moreover, the deformation processing function 34c is part of a deformation processing unit.

For example, the processing circuitry 34 reads a program corresponding to the determining function 34a from the memory 33 and executes the program, and thereby determines a position of a feature point of a stent graft in X-ray image data. In other words, the determining function 34a identifies the position of the feature point of the stent graft in X-ray image data. Moreover, for example, the processing circuitry 34 reads a program corresponding to the superimposed-image generating function 34b from the memory 33 and executes the program, and thereby generates a superimposed image in which a 3D model expressing the stent graft is superimposed on the X-ray image data at a position based on the position of the feature point. Furthermore, for example, the processing circuitry 34 reads a program corresponding to the deformation processing function 34c from the memory 33 and executes the program, and thereby deforms the 3D model expressing the stent graft based on the X-ray image data. Moreover, for example, the processing circuitry 34 reads a program corresponding to the output function 34d from the memory 33 and executes the program, and thereby outputs the superimposed image.

In the image processing apparatus 30 illustrated in FIG. 1, the respective processing functions are stored in a form of computer-executable program in the memory 33. The processing circuitry 34 is a processor that implements functions corresponding to the respective programs by reading the programs from the memory 33 and executing the programs. In other words, the processing circuitry 34 that has read a program is equivalent to having the function corresponding to the read program. Although it has been explained that the determining function 34a, the superimposed-image generating function 34b, the deformation processing function 34c, and the output function 34d are implemented by a single unit of the processing circuitry 34 with FIG. 1, the processing circuitry 34 may be configured by combining multiple independent processors, and may be configured such that the functions are implemented by the respective processors executing the programs. Moreover, the respective processing functions of the processing circuitry 34 may be implemented in a distributed manner with multiple processing circuits, or in an integrated manner with a single circuit, appropriately.

Figure 2:
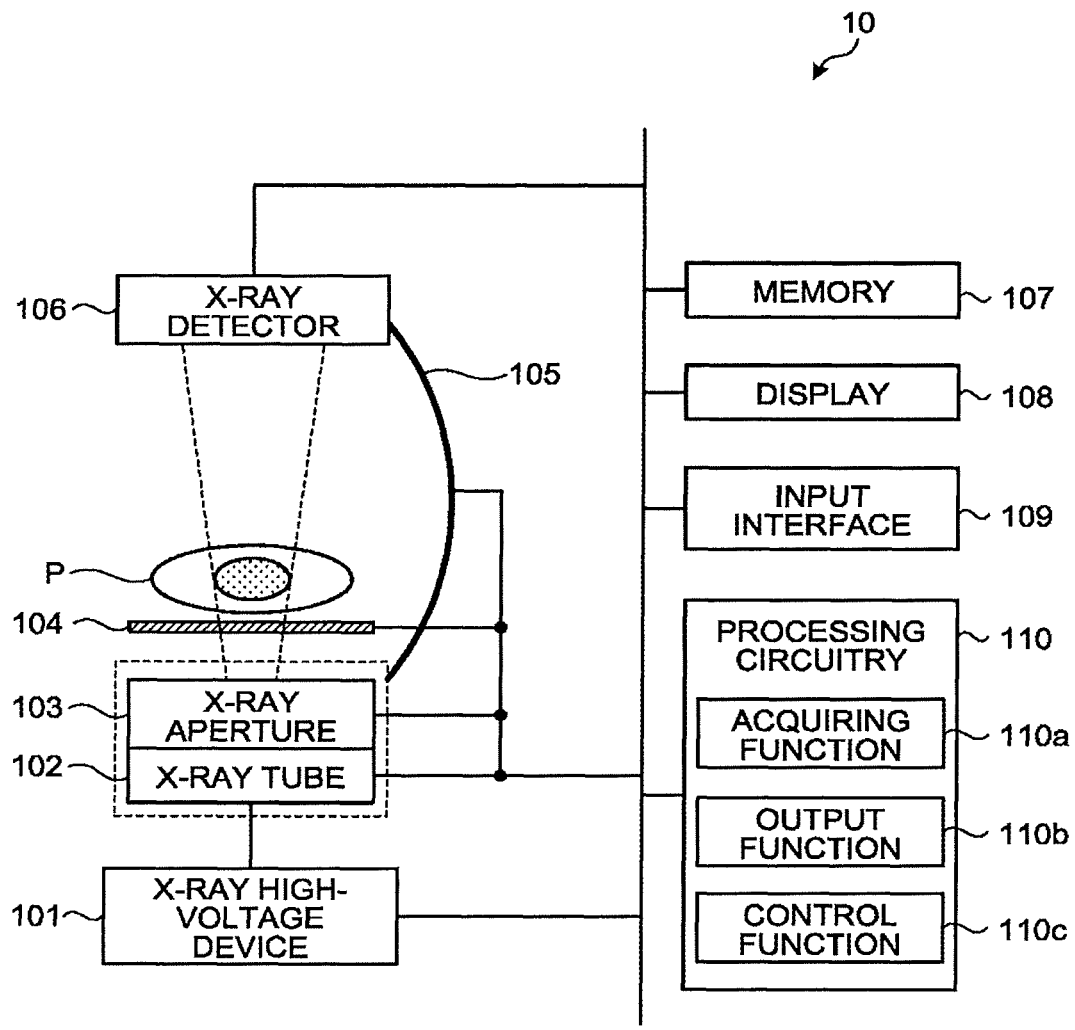
FIG. 2 is a block diagram illustrating an example of a configuration of an X-ray diagnostic apparatus according to the first embodiment.

Next, the X-ray diagnostic apparatus 10 that acquires X-ray image data is described, using FIG. 2. FIG. 2 is a block diagram illustrating an example of a configuration of the X-ray diagnostic apparatus 10 according to the first embodiment. As illustrated in FIG. 2, the X-ray diagnostic apparatus 10 includes an X-ray high-voltage device 101, an X-ray tube 102, an X-ray aperture 103, a tabletop 104, a C-arm 105, an X-ray detector 106, a memory 107, a display 108, an input interface 109, and processing circuitry 110.

The X-ray high-voltage device 101 supplies a high voltage to the X-ray tube 102, under control of the processing circuitry 110. For example, the X-ray high-voltage device 101 includes an electrical circuit, such as a transformer and a rectifier, and has a high-voltage generating device that generates a high voltage to be applied to the X-ray tube 102, and an X-ray control device that controls an output voltage according to an X-ray irradiated by the X-ray tube 102. The high-voltage generating device may be of a transformer type or of an inverter type.

The X-ray tube 102 is a vacuum tube that has a cathode (filament) that generates thermions, and an anode (target) that generates X-rays by thermionic impact. The X-ray tube 102 generates X-rays by emitting thermions from the cathode to the anode, using the high voltage supplied from the X-ray high-voltage device 101.

The X-ray aperture 103 includes a collimator that narrows an irradiation range of an X-ray that is generated by the X-ray tube 102, and a filter that adjusts the X-ray emitted from the X-ray tube 102.

The collimator in the X-ray aperture 103 has, for example, four slidable aperture blades. The collimator narrows an X-ray generated by the X-ray tube 102 by sliding the aperture blades, to irradiate the X-ray to the subject P. The aperture blades are plate-shaped members made from lead and the like, and are arranged near an X-ray irradiation outlet of the X-ray tube 102 to adjust the X-ray irradiation range.

The filter in the X-ray aperture 103 changes radiation properties of an X-ray that passes therethrough with its material and thickness to reduce soft ray components that are apt to be absorbed by the subject P, or to reduce high energy components that cause degradation in contrast of X-ray image data, for the purpose of reducing an exposure dose for the subject P and of improving the image quality of X-ray image data. Furthermore, the filter changes a dose and an irradiation range of an X-ray according to its material, thickness, position, and the like, to attenuate an X-ray such that the X-ray to be irradiated to the subject P from the X-ray tube 102 has a predetermined distribution.

For example, the X-ray aperture 103 has a driving mechanism, such as a motor and actuator, and controls irradiation of an X-ray by actuating the driving mechanism, under control of the processing circuitry 110 described later. For example, the X-ray aperture 103 adjusts the aperture of the aperture blades of the collimator by applying a driving voltage to the driving mechanism according to a control signal received from the processing circuitry 110, to control an irradiation range of an X-ray to be irradiated to the subject P. Moreover, for example, the X-ray aperture 103 adjusts a position of the filter by applying the driving voltage to the driving mechanism according to a control signal received from the processing circuitry 110, to control a distribution of X-ray dose to be irradiated to the subject P.

The tabletop 104 is a bed on which the subject P is laid, and is arranged on a not shown bedstead. The subject P is not included in the X-ray diagnostic apparatus 10. For example, the bedstead includes a driving mechanism, such as a motor and an actuator, and controls movement and tilt of the tabletop 104 by actuating the driving mechanism under control of the processing circuitry 110 described later. For example, the bedstead moves or tilts the tabletop 104 by applying a driving voltage to the driving mechanism according to a control signal received from the processing circuitry 110.

The C-arm 105 holds the X-ray tube 102 and the X-ray aperture 103, and the X-ray detector 106 so as to oppose to each other sandwiching the subject P. For example, the C-arm 105 has a driving mechanism, such as a motor and an actuator, and rotates or moves by actuating the driving mechanism under control of the processing circuitry 110 described later. For example, the C-arm 105 rotates or moves the X-ray tube 102 and the X-ray aperture 103, and the X-ray detector 106 relative to the subject P by applying a driving voltage to the driving mechanism according to a control signal received from the processing circuitry 110, to control an irradiation position and an irradiation angle of an X-ray. Although a case in which the X-ray diagnostic apparatus 10 is a single plane type has been described with FIG. 2 as an example, embodiments are not limited thereto. A case of a double plane type is also applicable.

The X-ray detector 106 is, for example, an X-ray flat-panel detector (FPD) that includes detecting devices arranged in a matrix. The X-ray detector 106 detects an X-ray that has irradiated from the X-ray tube 102 and passed through the subject P, and outputs a detection signal according to an amount of the detected X-ray to the processing circuitry 110. Note that the X-ray detector 106 may be an indirect conversion detector that includes a grid, a scintillator array, and an optical sensor, or may be a direct conversion detector that includes a semiconductor device converting an input X-ray into an electrical signal.

The memory 107 is implemented by, for example, a semiconductor memory, such as a RAM and a flash memory, a hard disk, an optical disk, or the like. For example, the memory 107 receives X-ray image data acquired by the processing circuitry 110 and stores the data. Moreover, the memory 107 stores programs corresponding to the respective functions that are read and executed by the processing circuitry 110. Note that the memory 107 may be implemented by a server group (cloud) connected with the X-ray diagnostic apparatus 10 through a network.

The display 108 displays various kinds of information. For example, the display 108 displays a GUI to receive an instruction from an operator and various kinds of X-ray images under control of the processing circuitry 110. For example, the display 108 is a liquid crystal display or a CRT display. The display 108 may be of a desktop type, or be constituted of a tablet terminal or the like that is capable of wireless communication with the processing circuitry 110.

The input interface 109 receives various kinds of input operation from the operator, and converts the received input operation into an electrical signal to output to the processing circuitry 110. For example, the input interface 109 is implemented by a mouse, a keyboard, a trackball, a switch, a button, a joystick, a touch pad that enables to make an input operation by a touch to an operating surface, a touch screen constituted of a display screen and a touch pad integrated, a non-contact input circuit that uses an optical sensor, a voice input circuit, or the like. The input interface 109 may be constituted of a tablet terminal or the like that is capable of wireless communication with the processing circuitry 110. Furthermore, the input interface 109 is not limited to one that includes a physical operation part, such as a mouse and a keyboard. For example, an electrical-signal processing circuit that receives an electrical signal corresponding to an input operation from an external input device provided separately from the X-ray diagnostic apparatus 10, and that outputs this electrical signal to the processing circuitry 110 is also included in examples of the input interface 109.

The processing circuitry 110 controls the overall operation of the X-ray diagnostic apparatus 10 by performing an acquiring function 110a, an output function 110b, and a control function 110c.

For example, the processing circuitry 110 acquires X-ray image data by reading and executing a program corresponding to the acquiring function 110a from the memory 107. For example, the acquiring function 110a controls the X-ray high-voltage device 101 to adjust a voltage supplied to the X-ray tube 102, and thereby controls a dose of an X-ray irradiated to the subject P or on/off of irradiation.

Furthermore, for example, the acquiring function 110a controls the operation of the X-ray aperture 103 to adjust the aperture of the aperture blades in the collimator, and thereby controls an irradiation range of an X-ray to be irradiated to the subject P. Moreover, the acquiring function 110a controls the operation of the X-ray aperture 103 and adjusts the position of the filter, and thereby controls the distribution of X-ray dose. Furthermore, the acquiring function 110a controls the operation of the C-arm 105 to rotate and move the C-arm 105. Moreover, the acquiring function 110*a* controls the operation of the bedstead, to move or tilt the tabletop 104.

Furthermore, the acquiring function 110*a* generates X-ray image data based on a detection signal received from the X-ray detector 106, and stores the generated X-ray image data in the memory 107. Moreover, the acquiring function 110*a* may perform various kinds of image processing with respect to the X-ray image data stored in the memory 107. For example, the acquiring function 110*a* performs noise reduction processing by an image processing filter, or scattered radiation correction with respect to the X-ray image data.

Moreover, the processing circuitry 110 reads and executes a program corresponding to the output function 110*b* from the memory 107, to cause the display 108 to display a GUI or an X-ray image. Furthermore, the output function 110*b* outputs X-ray image data to the image storage apparatus 20 or the image processing apparatus 30. Moreover, the processing circuitry 110 reads and executes a program corresponding to the control function 110*c* from the memory 107, to control various kinds of functions of the processing circuitry 110 based on an input operation received from the operator through the input interface 109.

In the X-ray diagnostic apparatus 10 illustrated in FIG. 2, the respective processing functions are stored in a form of computer-executable program in the memory 107. The processing circuitry 110 is a processor that implements functions corresponding to the respective programs by reading the programs from the memory 107 and executing the programs. In other words, the processing circuitry 110 that has read a program is equivalent to having the function corresponding to the read program. Although it has been explained that the acquiring function 110*a*, the output function 110*b*, and the control function 110*c* are implemented by a single unit of the processing circuitry 110 with FIG. 2, embodiments are not limited thereto. For example, the processing circuitry 110 may be configured by combining multiple independent processors, and may be configured such that the functions are implemented by the respective processors executing the respective programs. Moreover, the respective processing functions of the processing circuitry 110 may be implemented in a distributed manner with multiple processing circuits, or in an integrated manner with a single circuit, appropriately.

The term "processor" used in the above description signifies, for example, a circuit such as a central processing unit (CPU), a graphics processing unit (GPU), an application specific integrated circuit (ASIC), a programmable logic device (for example, a simple programmable logic device (SPLD), and a complex programmable logic device (CPLD)), and a field programmable gate array (FPGA). The processor reads and executes a program stored in the memory 33 or the memory 107, and thereby implements a function.

With FIG. 1 and FIG. 2, it has been described that one unit of the memory 33 or the memory 107 stores the programs corresponding to the respective processing functions. However, it may be configured such that multiple units of the memories 33 are arranged in a distributed manner, and that the processing circuitry 34 reads a corresponding program from the independent memory 33. Similarly, it may be configured such that multiple units of the memories 107 are arranged in a distributed manner, and that the processing circuitry 110 reads a corresponding program from the independent memory 107. Moreover, it may be configured to install the programs directly in a circuit in the processor, instead of storing the programs in the memory 33 and the memory 107. In this case, the processor implements a function by reading and executing a program installed in the circuit.

Furthermore, the processing circuitry 34 and the processing circuitry 110 may implement the functions by using a processor of an external device connected with the processing circuitry 34 therewith through a network. For example, the processing circuitry 34 implements the respective functions illustrated in FIG. 1 by reading and executing the programs corresponding to the respective functions from the memory 33, and by using a server group (cloud) connected with the image processing apparatus 30 through a network as a computing resource.

As above, the medical image-processing system 1 including the image processing apparatus 30 has been described. With such a configuration, the image processing apparatus 30 in the medical image-processing system 1 makes it easy to grasp a position of a device inside a subject by the processing performed by the processing circuitry 34.

As an example of the device, a stent graft is described herein. For example, a stent graft is manufactured according to a shape of a vessel of a treatment target region of the subject P. For example, in the stent graft indwelling for an aortic aneurysm, three-dimensional image data expressing a blood vessel shape of the subject P is acquired in preoperative treatment planning, and a stent graft is manufactured based on the three-dimensional image data.

For example, the acquiring function 110*a* in the X-ray diagnostic apparatus 10 performs rotational shooting to acquire projection data at predetermined frame rate while rotating the C-arm 105, and reconstructs three-dimensional image data that expresses a blood vessel shape of the subject P from the acquired projection data. As an example, the acquiring function 110*a* performs the rotational shooting with respect to the subject P in which a contrast agent has not been injected to a blood vessel, and acquires mask images at a predetermined frame rate. Moreover, the acquiring function 110*a* performs the rotational shooting with respect to the subject P in which a contrast agent has been injected to the blood vessel, and acquires contrast images at a predetermined frame rate. Next, the acquiring function 110*a* reconstructs three-dimensional image data that express the blood vessel shape of the subject P using subtraction image data that is obtained by subtraction between the mask image and the contrast image as projection data. As another example, the acquiring function 110*a* reconstructs three-dimensional image data using the mask image as projection data. Furthermore, the acquiring function 110*a* reconstructs three-dimensional image data using the contrast image as projection data. The acquiring function 110*a* then subtracts the two pieces of reconstructed three-dimensional image data, to generate three-dimensional image data expressing the blood vessel shape of the subject P.

Note that the three-dimensional image data expressing the blood vessel shape of the subject P may be acquired by the X-ray diagnostic apparatus 10, or by an X-ray diagnostic apparatus other than the X-ray diagnostic apparatus 10. Alternatively, it may be acquired by a medical diagnostic-imaging apparatus (for example, X-ray computed tomography (CT) and the like) other than the X-ray diagnostic apparatus.

Figure 3:
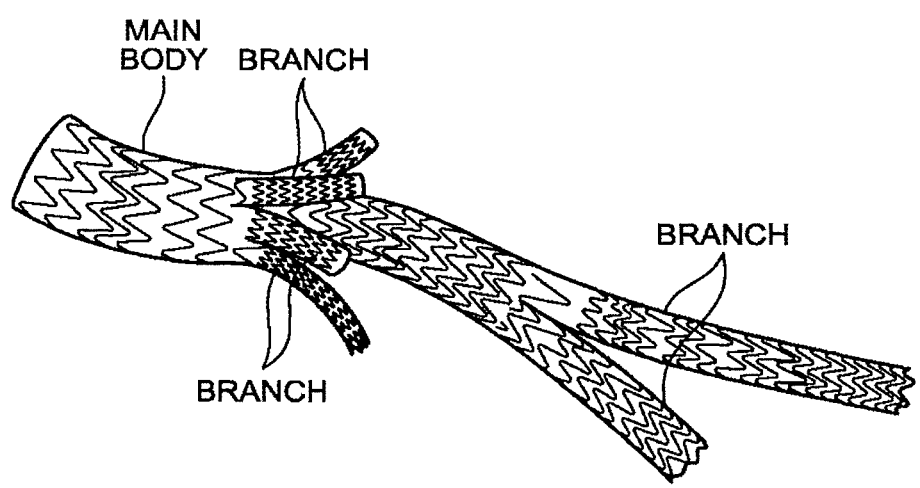
FIG. 3 illustrates an example of a stent graft according to the first embodiment.

For example, the stent graft has a main body and multiple branches. The main body illustrates in FIG. 3 is manufactured, for example, based on the shape of an aorta of the subject P. Moreover, for example, the branches illustrated in FIG. 3 are manufactured, for example, respectively based on the shape of various arteries (branched vessels) that branches off from the aorta. FIG. 3 illustrates an example of the stent graft according to the first embodiment.

For example, the stent graft is structured such that the main body and the branches are separable, and holes to put the branches in are arranged in the main body. In this case, in the stent graft indwelling, after the main body of the stent graft is indwelled in the aorta, the branches of the stent graft are indwelled so as to be inserted in the holes in the main body. The blood flow into an aortic aneurysm is thereby reduced to prevent dilation of the aortic aneurysm, but the blood flow into the respective arteries (branch vessels) branching off from the aorta is kept at the same time.

After the stent graft is manufactured, the operator performs the stent graft indwelling according to the preoperative plan. For example, the operator inserts the main body of the stent graft held in a catheter into a blood vessel of the subject P, to bring it to a position of the treatment target region (aortic aneurysm). At this time, the main body of the stent graft is housed in the catheter in a compressed state in a diameter direction.

The acquiring function 110a acquires X-ray image data of the treatment target region, and the output function 110b outputs the X-ray image data. For example, the acquiring function 110a acquires X-ray image data of the treatment target region in time series. Moreover, the output function 110b sequentially generates X-ray images for display based on the X-ray image data chronologically acquired, and displays the generated X-ray images sequentially on the display 108. Alternatively, the output function 110b sequentially outputs the X-ray image data acquired in time series to the image processing apparatus 30. In this case, the output function 34d in the image processing apparatus 30 sequentially generates X-ray images for display based on the X-ray image data acquired from the X-ray diagnostic apparatus 10, and sequentially displays the generated X-ray images on the display 32. Hereinafter, X-ray images that are sequentially displayed in parallel with acquisition of X-ray image data, or that are sequentially displayed in parallel with acquisition of X-ray image data from another device are also referred to as fluoroscopic images.

The operator indwells the main body of the stent graft at the position preoperatively planned while referring to a fluoroscopic image. Specifically, the operator pushes out the main body of the stent graft out from the catheter in a state in which the distal end of the catheter is positioned at the treatment target region. As illustrated in FIG. 3, the stent graft has a spring-shaped wire frame, and is housed in a catheter in a state in which the wire frame is compressed. Therefore, the main body of the stent graft pushed out from the catheter is expanded in the diameter direction by the elastic force of the wire frame, and indwelled in the aorta, being in contact with an inner wall of the blood vessel.

As described above, in the main body of the stent graft, the multiple holes to receive the branches fit therein are arranged. If the stent graft is indwelled in a state in which the positions of the holes in the main body of the stent graft and positions of entrances of the corresponding branch vessels are misaligned, the branches of the stent graft cannot be indwelled later, and a blood flow to the branch vessels can be inhibited. Therefore, the operator indwells the main body of the stent graft such that the positions of the holes in the main body of the stent graft and the positions of the entrances of the corresponding branch vessels match. However, the stent graft is usually not clearly shown in a fluoroscopic image, and it is not easy to grasp the position of the stent graft in a subject body.

The image processing apparatus 30 according to the first embodiment generates a superimposed image in which a 3D model expressing a stent graft is superimposed on X-ray image data, and thereby facilitates grasping the position of the stent graft in a subject body. Hereinafter, processing performed by the image processing apparatus 30 according to the first embodiment is described in detail.

The determining function 34a acquires X-ray image data acquired from the subject P in which a stent graft is inserted, and determines a position of a feature point of the stent graft in the acquired X-ray image data. Hereinafter, X-ray image data in which a position of a feature point is determined by the determining function 34a is referred to as X-ray image data I11. The X-ray image data I11 is an example of a first X-ray image.

For example, the determining function 34a sequentially acquires the X-ray image data I11 chronologically acquired by the X-ray diagnostic apparatus 10, and sequentially determines a position of a feature point of the stent graft in the acquired X-ray image data I11. The X-ray image data I11 may be X-ray image data that is acquired from the subject P in which a contrast agent has been injected and in which a blood vessel area of the subject P is contrasted, or may be X-ray image data that is acquired from the subject P in which a contrast agent is not injected.

Moreover, the X-ray image data I11 may be subtracted image data between X-ray image data that is acquired from the subject in which a stent graft has been inserted and X-ray image data that is acquired before the stent graft is inserted. In this case, in the X-ray image data I11, background components corresponding to bones, soft tissues, and the like are removed in the X-ray image data I11, and only the stent graft is rendered. Furthermore, when the X-ray image data I11 is subtracted image data based on the X-ray image data acquired from the subject P in which a contrast agent has been injected, the X-ray image data I11 renders the stent graft and the blood vessel area of the subject P contrasted by the contrast agent.

For example, the determining function 34a determines a position of a feature point by detecting a feature point of the stent graft in the X-ray image data I11. As an example, the determining function 34a detects a marker put on the stent graft in the X-ray image data I11. The marker is, for example, an X-ray impermeable metal put on the stent graft.

Figure 4A:
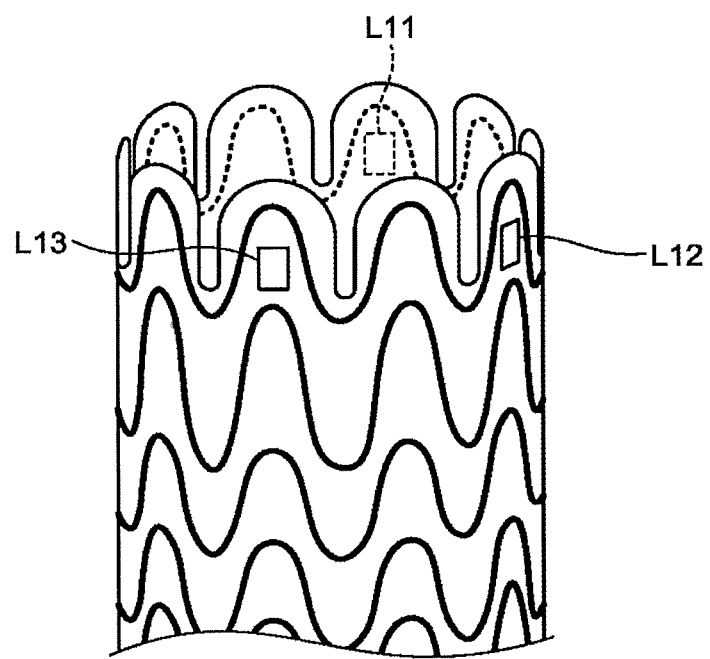
FIG. 4A illustrates an example of a marker of the stent graft according to the first embodiment.
Figure 4B:
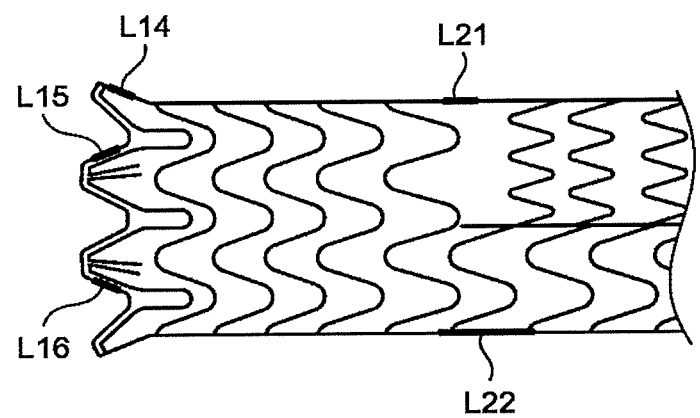
FIG. 4B illustrates an example of a marker of the stent graft according to the first embodiment.

For example, the stent graft has three markers (a marker L11, a marker L12, and a marker L13) at the distal end as illustrated in FIG. 4A. Moreover, for example, the stent graft has three markers (a marker L14, a marker L15, and a marker L16) at the distal end, and has two markers (a marker L21 and a marker L22) at middle portions as illustrated in FIG. 4B. FIG. 4A and FIG. 4B illustrate an example of a marker of the stent graft according to the first embodiment. For example, the determining function 34a performs pattern matching using a shape of a marker put on the stent graft with respect to the X-ray image data I11. Thus, the determining function 34a detects the markers in the X-ray image data I11.

For example, the operator pushes a distal end portion of the stent graft out of a catheter in a state in which the distal end of the catheter is positioned at a treatment target region. Thus, the stent graft is partially expanded as illustrated in a circular region expressed by a broken line in the X-ray image data I11 in FIG. 5. The determining function 34a detects the marker put on a distal end of the expanded stent graft in the X-ray image data I11, and determines positions of the marker L11, the marker L12, and the marker L13.

FIG. 5 is a diagram for describing generation of a superimposed image according to the first embodiment.

Moreover, the superimposed-image generating function 34b acquires a 3D model expressing the stent graft. For example, the superimposed-image generating function 34b acquires a 3D data (computer-aided design (CAD) data or the like) that is used when manufacturing the stent graft as a 3D model M. Furthermore, for example, the superimposed-image generating function 34b acquires the 3D model M by performing modeling by imaging the manufactured stent graft from multiple angles by an optical camera, an X-ray CT apparatus, the X-ray diagnostic apparatus 10, or the like. Hereinafter, the 3D model M acquired by the superimposed-image generating function 34b is also referred to as 3D model M1.

As illustrated in FIG. 5, the 3D model M1 includes a marker L11', a marker L12', and a marker L13'. For example, the marker L11', the marker L12', and the marker L13' are information that indicates positions of the respective three markers (the marker L11, the marker L12, the marker L13) put on the stent graft. Furthermore, the marker L11', the marker L12', and the marker L13' may be information that indicates shapes, sizes, and the like of the respective three markers (the marker L11, the marker L12, the marker L13) put on the stent graft.

For example, the superimposed-image generating function 34b acquires the 3D model M1 described above before the stent graft indwelling is started, and stores it in the memory 33. After the stent graft indwelling is started, the superimposed-image generating function 34b reads the 3D model M1 from the memory 33 and superimposes it on the X-ray image data I11, to generate a superimposed image.

The superimposed-image generating function 34b superimposes the 3D model M1 at a position based on the position determined by the determining function 34a in the X-ray image data I11 as illustrated in FIG. 5. Specifically, the superimposed-image generating function 34b superimposes the 3D model M1 on the X-ray image data I11 such that the marker L11' in the 3D model M1 matches with the position of the marker L11 determined in the X-ray image data I11, the marker L12' in the 3D model M1 matches with the position of the marker L12 determined in the X-ray image data I11, and the marker L13' in the 3D model M1 matches with the position of the marker L13 determined in the X-ray image data I11.

More specifically, the superimposed-image generating function 34b determines correspondence between the markers determined in the X-ray image data I11 and the markers in the 3D model M1, respectively. The marker L11, the marker L12, and the marker L13 are put on the stent graft at nonuniform intervals as illustrated in FIG. 4A. Therefore, the superimposed-image generating function 34b can determine correspondence between the marker L11, the marker L12, the marker L13 and the marker L11', the marker L12', and the marker L13' uniquely.

That is, when superimposing the 3D model M1 on the X-ray image data such that the marker L11' matches with the position of the marker L12, because the interval between the marker L12 and the marker L11 and the interval between the marker L11' and the marker L13' are different, the marker L13' does not match with the position of the marker L11 (the marker L13 and the marker L12' do not match with each other, either). Similarly, when superimposing the 3D model M1 on the X-ray image data I11 to match the marker L11' with the position of the marker L13, the marker L12' does not match with the position of the marker L11, and the marker L13' does not match with the position of the marker L12, either.

On the other hand, when superimposing the 3D model M1 on the X-ray image data I11 to match the marker L11' with the position of the marker L11, the marker L12' matches with the position of the marker L12, and the marker L13' matches with the position of the marker L13. Therefore, the superimposed-image generating function 34b can determine that the marker L11' corresponds with the marker L11, the marker L12' corresponds with the marker L12, and the marker L13' corresponds with the marker L13.

Note that the method of uniquely determining correspondence between respective markers that have been determined in the X-ray image data and respective markers in the 3D model M1 is not limited to the example described above. For example, when shapes and sizes of markers put on a stent graft differ from one another, the superimposed-image generating function 34b can determine correspondence uniquely by comparing the shapes and the sizes of the respective markers detected in the X-ray image data I11 and the shapes and sizes of markers in the 3D model M1.

Furthermore, to match the marker L11' with the position of the marker L11, the marker L12' with the position of the marker L12, and the marker L13' with the position of the marker L13, the superimposed-image generating function 34b moves in a parallel direction, enlarges or reduces, or rotates the 3D model M1 with respect to the X-ray image data I11. Thus, the superimposed-image generating function 34b generates a superimposed image I21 illustrated in FIG. 5 by superimposing the 3D model M1 on the X-ray image data I11 at the position and the orientation based on the positions of the markers determined by the determining function 34a.

With FIG. 5, the case in which the determining function 34a determines positions of three feature points in the X-ray image data I11 has been described, but the number of feature points to be determined by the determining function 34a in the X-ray image data I11 is not limited to three.

For example, as illustrated in FIG. 4B, when three markers (the marker L14, the marker L15, and the marker L16) are put on at the distal end of a stent graft, and two markers (the marker L21 and the marker L22) are put on at middle portions, the determining function 34a determines positions three or five feature points in the X-ray image data I11.

That is, when only a distal end portion at which the marker L14, the marker L15, and the marker L16 are put is expanded out of the stent graft is expanded, the determining function 34a detects the three markers put at the distal end portion of the stent graft in the X-ray image data I11 and determines the positions. Moreover, when a portion up to the middle portion, in addition to the distal end portion, is expanded, the determining function 34a detects the five markers put on at the distal end and the middle portion of the expanded stent graft in the X-ray image data and determines the positions. Furthermore, when markers are put on at a portion other than the distal end or the middle portion (for example, a branch portion) and the stent graft is expanded up to a portion at which these markers are put on, the determining function 34a detects the markers put on at the expanded portion and determines the positions. As the number of feature points, positions of which are determined by the determining function 34a increases, the superimposed-image generating function 34b can improve the accuracy in superimposing the 3D model M1 on the X-ray image data I11 at a position and an orientation based on the positions of the feature points.

The case in which the determining function 34a determines positions of three or more feature points has been described, but the number of positions of feature points to be determined by the determining function 34a in the X-ray image data I11 may be less than three. For example, when two markers are put on a stent graft, the determining function 34a determines positions of the two markers in the X-ray image data I11. When the markers put on the stent graft show different shapes depending on a direction (for example, when the marker has a planar shape or a rod shape), the superimposed-image generating function 34b superimposes the 3D model M1 on the X-ray image data I11 such that the positions, shapes, and sizes of the two markers match with each other, respectively. That is, the superimposed-image generating function 34b superimposes the 3D model M1 on the X-ray image data I11 at the position and the orientation based on the positions of the determined two feature points.

The output function 34d outputs the superimposed image I21 generated by the superimposed-image generating function 34b. For example, the output function 34d displays the generated superimposed image I21 on the display 32. Moreover, for example, the output function 34d outputs the superimposed image I21 to the X-ray diagnostic apparatus 10. In this case, the output function 110b in the X-ray diagnostic apparatus 10 displays the superimposed image I21 acquired from the image processing apparatus 30 on the display 108.

The superimposed image I21 may be replaced with an X-ray image for display based on the X-ray image data I11 to be displayed, or may be displayed together with an X-ray image for display based on the X-ray image data I11. For example, the output function 110b may display the superimposed image I21 and an X-ray image for display based on the X-ray image data I11 in parallel on one display, or may display them on respective different displays.

When the X-ray image data I11 are chronologically acquired, the superimposed-image generating function 34b sequentially generates the superimposed images I21 in parallel with acquisition of the X-ray image data I11, and the output function 34d sequentially outputs the generated superimposed images I21. When the stent graft moves in a blood vessel of the subject P, operated by the operator, or the like, the 3D model M1 also moves or rotates in the superimposed image I21, following the movement of the markers. Therefore, the operator can grasp the position and direction (orientation) of the stent graft to be operated inside a blood vessel of the subject P.

The superimposed-image generating function 34b may generate the superimposed image I21, superimposing the 3D model M1 to be displayed in a semitransparent state over the X-ray image data I11. For example, in FIG. 5, part of the catheter rendered in the X-ray image data I11 is hidden by the 3D model M1. The superimposed-image generating function 34b facilitates grasping of the position and the orientation of the stent graft in a subject body by making the 3D model M1 semitransparent, and makes an area overlapping with the 3D model M1 out of the X-ray image data I11 visible at the same time.

With FIG. 5, the case in which the superimposed image I21 is generated by superimposing the 3D model M1 on the X-ray image data I11 has been described, but embodiments are not limited thereto. For example, the deformation processing function 34c may deform the 3D model M1, such as the 3D model M1, based on the X-ray image data I11, and superimpose the 3D model M subjected to deformation on the X-ray image data I11.

For example, the deformation processing function 34c acquires a blood vessel shape of the subject P in which a stent graft is inserted based on the X-ray image data I11, and deforms the 3D model M according to the acquired blood vessel shape. Hereinafter, the 3D model M deformed according to a blood vessel shape is referred to as a 3D model M2.

For example, the deformation processing function 34c acquires a blood vessel shape from the X-ray image data acquired in a state in which a contrast agent has been injected to the vessel of the subject P including a treatment target region, after a stent graft is inserted into the treatment target region (aortic aneurysm or the like). As an example, the deformation processing function 34c extracts a region having a pixel value larger than a threshold from the X-ray image data I11 that has been acquired in a state in which a positive contrast agent (iodine contrast agent, or the like) is injected as a blood vessel region, and acquires an outline of the blood vessel region as a blood vessel shape.

The deformation processing function 34c then deforms the 3D model M according to the acquired blood vessel shape, to generate the 3D model M2. For example, the deformation processing function 34c generates the 3D model M2 by reducing or enlarging the 3D model M1 in a diameter direction, or bending along a core line. In this case, the 3D model M2 shows a shape close to the stent graft after indwelling.

Because the stent graft is indwelled in a state of being in contact with an inner wall of a blood vessel, the stent graft after indwelling has a shape according to the blood vessel shape of the subject P. Accordingly, even if the stent graft is manufactured based on three-dimensional image data expressing the blood vessel shape of the subject P or the like, the blood vessel shape of the subject P at the time of indwelling the stent graft is not necessarily the same as the blood vessel shape at the time of acquisition of the three-dimensional image data (at the preoperative planning). Therefore, the shape of the 3D model M1 expressing the shape of the stent graft at the time of preoperative planning does not necessarily match with the shape of the stent graft after indwelling. On the other hand, the deformation processing function 34c acquires the blood vessel shape of the subject P in which the stent graft is inserted based on the X-ray image data I11, and deforms the 3D model M1 based on the acquired blood vessel shape, and thereby makes the 3D model M1 close to the shape of the stent graft after indwelling.

Furthermore, the superimposed-image generating function 34b superimposes the 3D model M2 subjected to deformation on the X-ray image data I11 to generate a superimposed image I22. Moreover, the output function 34d outputs the superimposed image I22 generated by the superimposed-image generating function 34b. For example, when the X-ray image data I11 is chronologically acquired, the superimposed-image generating function 34b sequentially generates the superimposed image I22 in parallel with acquisition of the X-ray image data I11, and the output function 34d sequentially outputs the generated superimposed images I22. Thus, the operator can grasp a position and an orientation of the stent graft operated in a blood vessel of the subject P easily. Furthermore, the operator can determine whether to indwell the stent graft at a current position by referring to the 3D model M2 that is close to the shape of the stent graft after indwelling.

As another example, the deformation processing function 34c acquires an expansion state of the stent graft out of the catheter based on the X-ray image data I11, and deforms the 3D model M, such as the 3D model M1 and the 3D model M2, according to the acquired expansion state. Hereinafter, the 3D model M that has been deformed according to an expansion state of a stent graft is referred to as a 3D model M3.

For example, the determining function 34a determines positions of the respective three markers (the marker L11, the marker L12, and the marker L13) put on at the distal end of the stent graft in the X-ray image data I11 as illustrated in FIG. 6. Moreover, the determining function 34a determines a distal end position of the catheter in the X-ray image data I11 as illustrated in FIG. 6. FIG. 6 is a diagram for describing generation of a superimposed image according to the first embodiment.

Next, the deformation processing function 34c moves in a parallel direction with respect to the X-ray image data I11, enlarges or reduces, or rotates the 3D model M1 with respect to the X-ray image data I11 such that the marker L11' matches with the position of the marker L11, the marker L12' matches with the position of the marker L12, and the marker L13' matches with the position of the marker L13. Thus, the deformation processing function 34c determines a position corresponding to the position of the distal end of the catheter in the 3D model M1.

A portion (hereinafter, first portion) from the marker L11', the marker L12', and the marker L13' to the position of the distal end in the 3D model M1 corresponds to the portion expanded out from the catheter out of the stent graft. On the other hand, a portion (hereinafter, second portion) from the marker L11', the marker L12', and the marker L13' to a portion opposite to the position of the distal end of the catheter in the 3D model M1 corresponds to a portion remaining inside the catheter out of the stent graft.

Accordingly, by deforming the 3D model M1 such that the second portion is omitted, the deformation processing function 34c generates a 3D model M31. Thus, the 3D model M31 shows a shape close to the expanded portion of the stent graft. Moreover, as illustrated in FIG. 6, the deformation processing function 34c may generate the 3D model M31 by deforming the 3D model M1 such that the second portion is omitted, and that one end close to the position of the distal end of the catheter of the first portion becomes thinner toward the position of the distal end of the catheter. The 3D model M31 is an example of the 3D model M3.

Furthermore, the superimposed-image generating function 34b superimposes the deformed 3D model M31 on the X-ray image data I11 as illustrated in FIG. 6, and thereby generates a superimposed image I23. Moreover, the output function 34d outputs the superimposed image I23 generated by the superimposed-image generating function 34b. For example, when the X-ray image data I11 is chronologically acquired, the superimposed-image generating function 34b sequentially generates the superimposed image I23 in parallel with acquisition of the X-ray image data I11, and the output function 34d sequentially outputs the generated superimposed images I23. Thus, the operator can grasp a position and an orientation of the stent graft operated inside a blood vessel of the subject P easily. Furthermore, the operator can grasp a current expansion state of the stent graft by referring to the 3D model M31 that is close to the shape of an expanded portion of the stent graft.

Another example of the 3D model M3 is described. For example, the deformation processing function 34c may generate the 3D model M3 by acquiring an expansion state of a stent graft out to a catheter based on intervals between positions of feature points determined in the X-ray image data I11, and by deforming the 3D model M1 according to the acquired expansion state.

For example, as illustrated in FIG. 4B, when five markers (the marker L14, the marker L15, the marker L16, the marker L21, and the marker L22) are put on a stent graft, the determining function 34a detects the five markers in the X-ray image data I11, and determines the positions.

Next, the deformation processing function 34c moves in a parallel direction with respect to the X-ray image data I11, enlarges or reduces, or rotates the 3D model M1 such that three corresponding markers in the 3D model M1 match with positions of three markers out of the positions of the five markers determined in the X-ray image data I11. Furthermore, the deformation processing function 34c partially deforms the 3D model M1 such that two corresponding markers in the 3D model M1 match with positions of other two markers determined in the X-ray image data I11. A 3D model M32 is an example of the 3D model M3.

There is a case in which a stent graft does not expand as preoperatively planned as a result of expanding the stent graft inside a blood vessel of the subject P. For example, when a shape of the blood vessel of the subject P at the time of preoperative planning is not the same as a shape at the time of performing the stent graft indwelling, or when a blood vessel of the subject P is harder or softer than expected, or the stent graft expands much more than expected at the preoperative planning, or does not expand as much as expected. Therefore, the 3D model M1 expressing the shape of the stent graft at the time of preoperative planning and the shape of the stent graft expanded in a blood vessel of the subject P is not necessarily the same. On the other hand, the deformation processing function 34c can make the 3D model M1 close to the shape of the stent graft expanded in a blood vessel of the subject P by acquiring an expansion state of the stent graft out of a catheter based on the X-ray image data I11, and by deforming the 3D model M1 according to the acquired expansion state.

Furthermore, the superimposed-image generating function 34b superimposes the deformed 3D model M32 on the X-ray image data I11, and thereby generates a superimposed image I24. Moreover, the output function 34d outputs the superimposed image I24 generated by the superimposed-image generating function 34b. For example, when the X-ray image data I11 is chronologically acquired, the superimposed-image generating function 34b sequentially generates the superimposed image I24 in parallel with acquisition of the X-ray image data I11, and the output function 34d sequentially outputs the generated superimposed images I24. Thus, the operator can grasp a position and an orientation of the stent graft operated inside a blood vessel of the subject P easily. Furthermore, the operator can grasp a current expansion state of the stent graft by referring to the 3D model M32 that is close to the shape of the stent graft expanded inside the blood vessel of the subject P.

Figure 7:
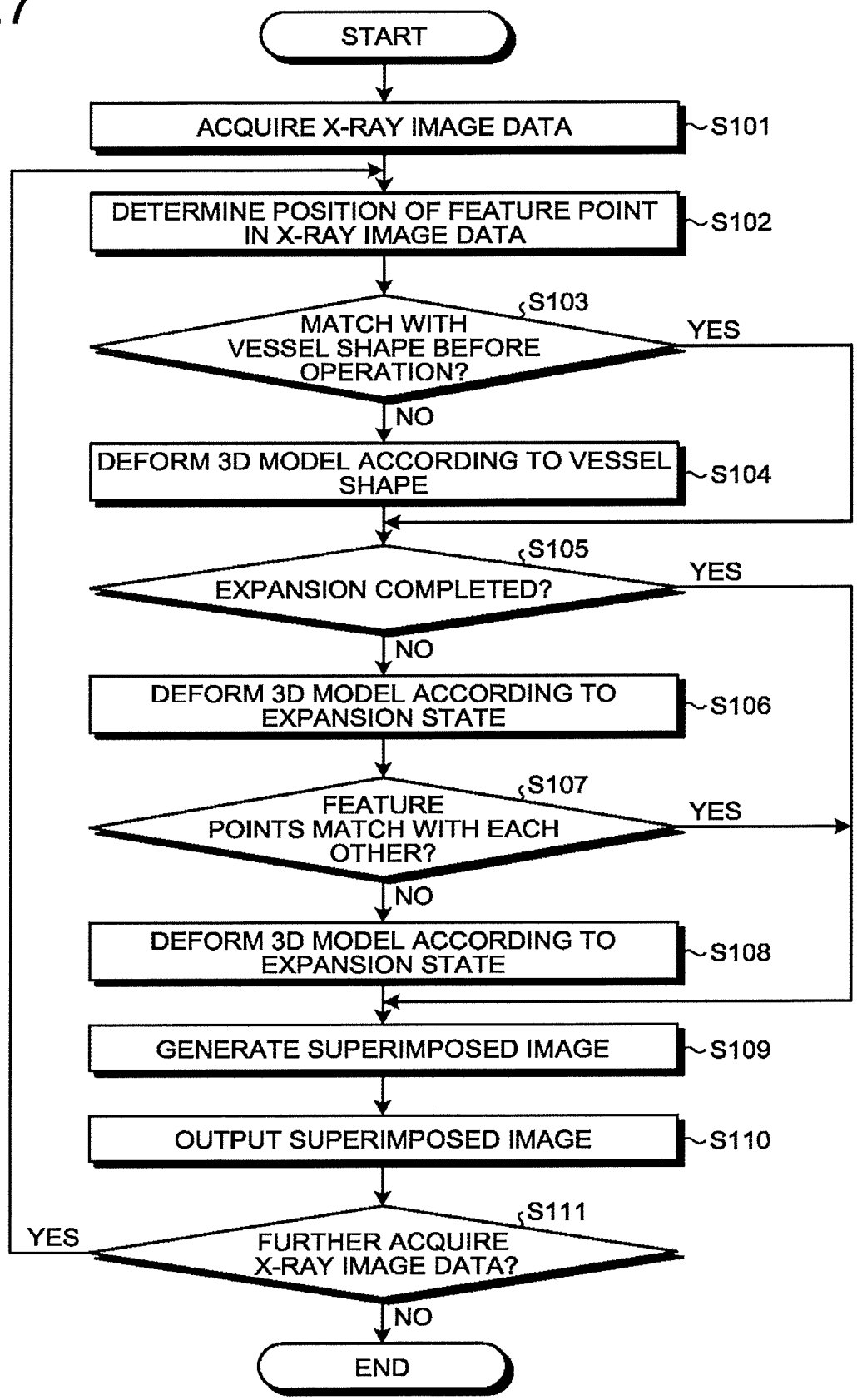
FIG. 7 is a flowchart for describing a flow of a procedure of processing performed by an image processing apparatus according to the first embodiment.

Next, an example of a procedure of processing performed by the image processing apparatus 30 is described by using FIG. 7. FIG. 7 is a flowchart for describing a flow of a procedure of the processing performed by the image processing apparatus 30 according to the first embodiment. Step S101, step S102, and step S111 are steps corresponding to the determining function 34a. Step S109 is a step corresponding to the superimposed-image generating function 34b. Step S103, step S104, step S105, step S106, step S107, and step S108 are steps corresponding to the deformation processing function 34c. Step S110 is a step corresponding to the output function 34d.

First, the processing circuitry 34 acquires the X-ray image data I11 (step S101), and determines a position of a feature point of a stent graft in the acquired X-ray image data I11 (step S102).

Next, the processing circuitry 34 acquires a blood vessel shape of the subject P in which the stent graft is inserted based on the X-ray image data I11, and determines whether the acquired blood vessel shape matches with a blood vessel shape before operation (for example, at the time of acquisition of three-dimensional image data to manufacture the stent graft) (step S103). When the blood vessel shapes do not match with each other (step S103: NO), the processing circuitry 34 deforms the 3D model M according to the blood vessel shape acquired based on the X-ray image data I11 (step S104).

When the blood vessel shape acquired based on the X-ray image data I11 matches with the blood vessel shape before operation (step S103: YES), or after step S104, the processing circuitry 34 determines whether expansion of the stent graft has been completed (step S105). When expansion of the stent graft has not been completed (step S105: NO), the processing circuitry 34 deforms the 3D model M according to the expansion state (step S106). For example, the processing circuitry 34 determines a position corresponding to a position of the distal end of the catheter in the 3D model M, and deforms the 3D model M such that a portion corresponding to a portion remaining inside the catheter is omitted.

Next, the processing circuitry 34 determines whether multiple feature points in the 3D model M match with positions of multiple feature points determined in the X-ray image data I11 (step S107). When the feature points do not match therewith (step S107: NO), the processing circuitry 34 deforms the 3D model M according to the expansion state (step S108). For example, the processing circuitry 34 moves in a parallel direction with respect to the X-ray image data I11, enlarges or reduces, or rotates the 3D model M such that corresponding feature points in the 3D model M match with part of the feature points determined in the X-ray image data I11. Thereafter, the processing circuitry 34 deforms part of the 3D model M such that corresponding feature points in the 3D model match with the positions of the other determined feature points.

When expansion of the stent graft has been completed (step S105: YES), if the markers and the feature points match with each other (step S107: YES), or after step S108, the processing circuitry 34 superimposes the 3D model M on the X-ray image data I11 at a position based on the positions of the determined feature points, to generate a superimposed image (step S109), and outputs the generated superimposed image (step S110). The processing circuitry 34 determines whether more piece of the X-ray image data I11 is acquired (step S111). When more piece of the X-ray image data I11 is acquired (step S111: YES), the processing circuitry 34 shifts to Step S102 again. On the other hand, when the X-ray image data I11 is not acquired (step S111: NO), the processing circuitry 34 ends the processing.

As described above, according to the first embodiment, the determining function 34a determines positions of feature points of a stent graft in the X-ray image data I11. Moreover, the superimposed-image generating function 34b generates a superimposed image that is obtained by superimposing the 3D model M expressing the stent graft on the X-ray image data I11. The superimposed-image generating function 34b superimposes the 3D model M on the X-ray image data I11 at a position based on the positions of the determined feature points. Therefore, the image processing apparatus 30 according to the first embodiment can make it easy to grasp a position of a stent graft in the subject P.

Moreover, according to the first embodiment, the determining function 34a determines positions of multiple feature points in the X-ray image data I11. Furthermore, the superimposed-image generating function 34b superimposes the 3D model M at a position and an orientation based on the positions of the determined feature points. Therefore, the image processing apparatus 30 according to the first embodiment can make it easy to grasp a position and an orientation of a stent graft in the subject P.

In the first embodiment described above, the 3D model M1, the 3D model M2, and the 3D model M3 expressing a shape of a stent graft have been described as an example of the 3D model expressing a stent graft. Meanwhile, in the second embodiment, a 3D model M4 that indicates a position and an orientation of a branch of a stent graft is described as an example of the 3D model M.

The image processing apparatus 30 according to the second embodiment has a configuration similar to that of the image processing apparatus 30 illustrated in FIG. 1, but part of the processing performed by the superimposed-image generating function 34b differs therefrom. Accordingly, the reference symbols same as those in FIG. 1 are assigned to structures similar to the structures described in the first embodiment, and description thereof is omitted.

For example, the superimposed-image generating function 34b first acquires the 3D model M1 expressing the shape of a stent graft. Next, the superimposed-image generating function 34b determines a position of a branch of the stent graft in the 3D model M1. For example, the superimposed-image generating function 34b determines a position of a hole that is arranged in a main body of the stent graft into which the branch is fit, as the position of the branch. Next, the superimposed-image generating function 34b determines an orientation of the branch of the stent graft in the 3D model M1. For example, the superimposed-image generating function 34b determines a vertical direction included in a plane surrounded by an outline (rim) of the hole in the main body, as the orientation of the branch.

Figure 8:
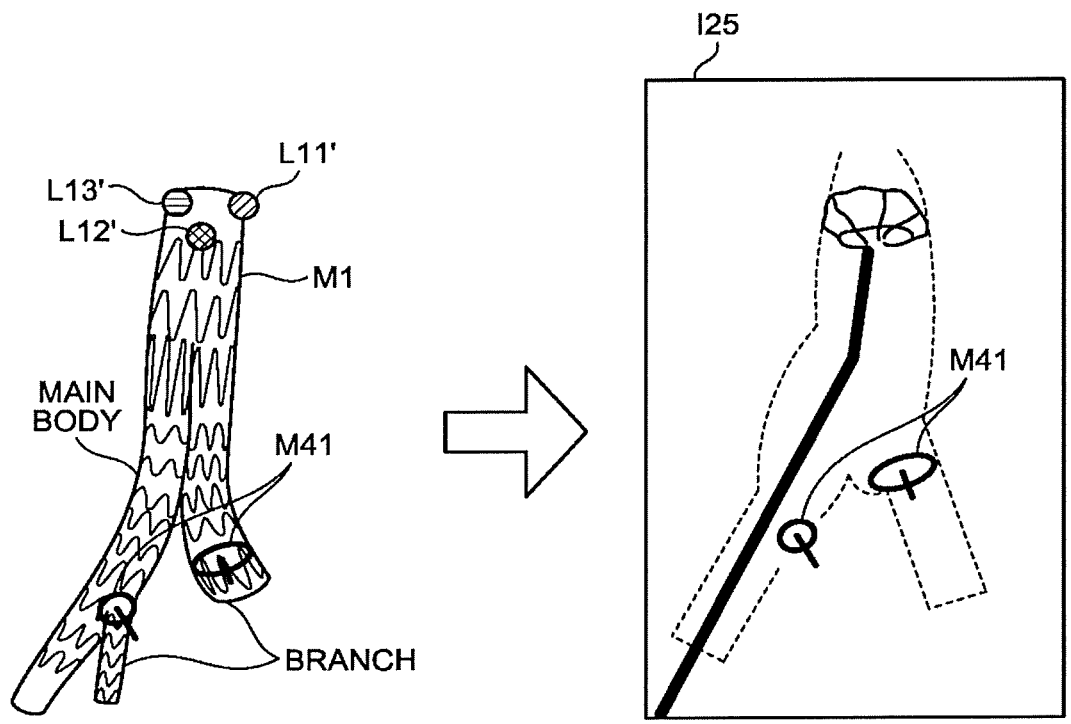
FIG. 8 is a diagram for describing generation of a superimposed image according to a second embodiment.

The superimposed-image generating function 34b then generates the 3D model M4 based on the determined position and orientation of the branch. For example, the superimposed-image generating function 34b generates the 3D model M41 that indicates the position and the orientation of the branch of the stent graft as illustrated in FIG. 8. FIG. 8 is a diagram for describing generation of a superimposed image according to the second embodiment.

The 3D model M41 illustrated in FIG. 8 includes an ellipse indicating the outline (the position of the branch) of the hole in the main body. Moreover, the 3D model M41 includes a line segment indicating the vertical line (orientation of the branch) that passes through a center of the plane surrounded by the outline of the hole in the main body and that is perpendicular to this plane. For example, the superimposed-image generating function 34b superimposes the 3D model M41 on the X-ray image data at a position based on the feature points determined by the determining function 34a, to generate a superimposed image I25 as illustrated in FIG. 8. Furthermore, the output function 34d outputs the superimposed image I25 generated by the superimposed-image generating function 34b.

Figure 9:
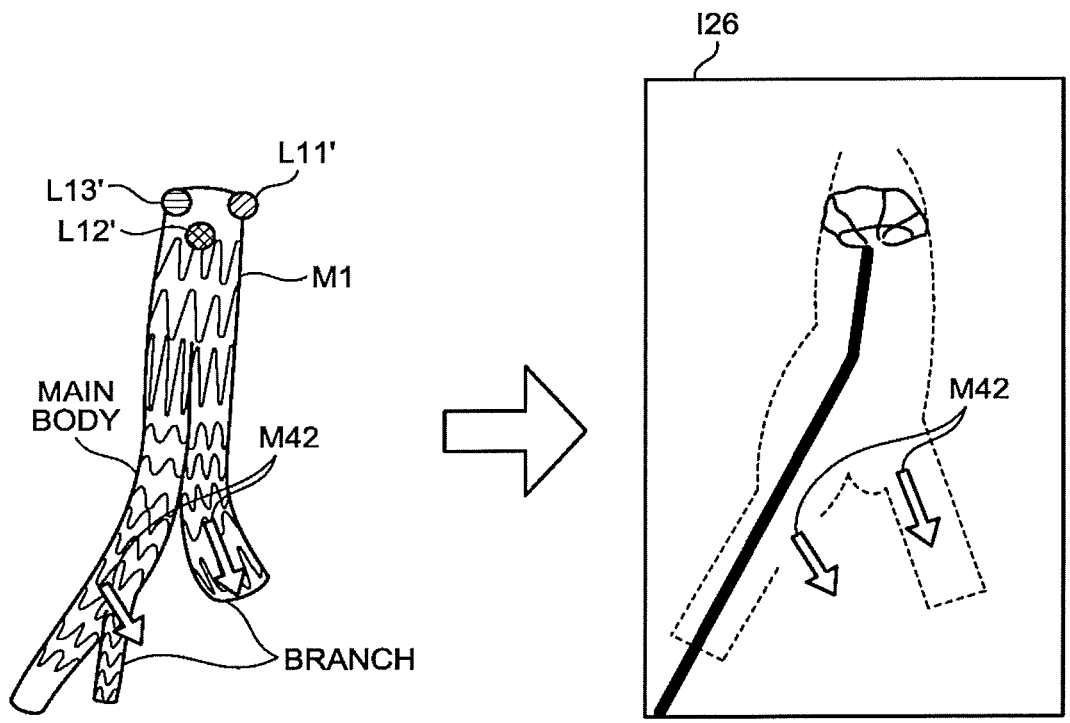
FIG. 9 is a diagram for describing generation of a superimposed image according to the second embodiment.

As another example, the superimposed-image generating function 34b generates a 3D model M42 that indicates a position and an orientation of a branch of a stent graft as illustrated in FIG. 9. FIG. 9 is a diagram for describing generation of a superimposed image according to the second embodiment.

The 3D model M42 illustrated in FIG. 9 includes an arrow that passes through a center of a plane surrounded by an outline of a hole in a main body, and that directs a direction perpendicular to this plane, as a figure that indicates a position and an orientation of the branch. For example, the superimposed-image generating function 34b superimposes the 3D model M42 on the X-ray image data I11 at a position based on the position of the feature points determined by the determining function 34a, to generate a superimposed image I26. Moreover, the output function 34d outputs the superimposed image I26 generated by the superimposed-image generating function 34b.

In FIG. 8 and FIG. 9, two examples of the 3D model M41 and the 3D model M42 have been illustrated as an example of the 3D model M4, but embodiments are not limited thereto. That is, the superimposed-image generating function 34b can generate the 3D model M4 by using any figure of image that indicates a position and an orientation of a branch of a stent graft. Moreover, the superimposed-image generating function 34b may generate the 3D model M4 indicating an orientation of a branch of a stent graft by using colors and shadows.

As described above, the superimposed-image generating function 34b according to the second embodiment generates a superimposed image in which the 3D model M4 indicating a position and an orientation of a branch of a stent graft is superimposed on the X-ray image data I11. Therefore, the image processing apparatus 30 according to the second embodiment can make it easy to grasp a position and an orientation of a stent graft in a subject.

The superimposed-image generating function 34b may generate a superimposed image by superimposing the 3D model M (3D model M1, or the like) indicating a shape of a stent graft and the 3D model M4 indicating a position and an orientation of a branch of the stent graft on the X-ray image data I11. In this case, the image processing apparatus 30 can make it further easy to grasp a position and an orientation of a stent graft in a subject by presenting different types of the 3D models M to the operator.

On the other hand, when only the 3D model M4 is superimposed on the X-ray image data I11, the image processing apparatus 30 can reduce a region in which the 3D model overlaps in the X-ray image data I11. For example, in the superimposed image I21 illustrated in FIG. 5, the 3D model M1 overlaps part of the catheter rendered in the X-ray image data I11. On the other hand, in the superimposed image I25 in FIG. 8 or the superimposed image I26 in FIG. 9, the entire part of the catheter rendered in the X-ray image data I11 appears. The image processing apparatus 30 may display multiple various superimposed images described above on one or more than one display, or may display the images, switching thereamong according an input operation made by an operator, or the like.

In the first to the second embodiments, the case in which the 3D model M is superimposed on the X-ray image data I11 (the first X-ray image) has been described. Meanwhile, in a third embodiment, a case in which the 3D model M is superimposed on X-ray image data (second image data) different from the X-ray image data I11 is described.

The image processing apparatus 30 according to the third embodiment has a configuration similar to that of the image processing apparatus 30 illustrated in FIG. 1, but part of processing performed by the superimposed-image generating function 34b differs therefrom. Accordingly, the reference symbols same as those in FIG. 1 are assigned to structures similar to the structures described in the first embodiment, and description thereof is omitted.

The superimposed-image generating function 34b acquires X-ray image data different from the X-ray image data I11. The superimposed-image generating function 34b may generate X-ray image data different from the X-ray image data I11 based on the X-ray image data I11, or may acquire X-ray image data different from the X-ray image data I11 from another apparatus (the X-ray diagnostic apparatus 10).

For example, the acquiring function 110a chronologically acquires multiple pieces of X-ray image data. Moreover, the output function 110b sequentially outputs the X-ray image data chronologically acquired to the image processing apparatus 30. The determining function 34a determines positions of feature points of a stent graft in the X-ray image data I11 that is acquired by the acquiring function 110a and is output from the output function 110b. For example, the determining function 34a determines positions of the marker L11, the marker L12, and the marker L13 in the X-ray image data I11.

Moreover, the superimposed-image generating function 34b determines, in X-ray image data I12 that is acquired later than the X-ray image data I11 by the acquiring function 110a and is output by the output function 110b, a position corresponding to the position of the feature point determined in the X-ray image data I11. The X-ray image data I12 is an example of the second image data.

For example, the superimposed-image generating function 34b determines positions corresponding to the positions of the marker L11, the marker L12, and the marker L13 in the X-ray image data I11 as positions of the marker L11, the marker L12, and the marker L13 in the X-ray image data I12 because the X-ray image data I11 and the X-ray image data I12 show substantially the same area in the subject P. Alternatively, the superimposed-image generating function 34b determines positions in the X-ray image data I12 corresponding to the positions determined in the X-ray image data I11 by registering the X-ray image data I11 and the X-ray image data I12.

The superimposed-image generating function 34b then superimposes the 3D model M on the X-ray image data I12 at a position based on the positions of the feature points determined by the determining function 34a, to generate a superimposed image I27. Moreover, the output function 34d the generated superimposed image I27 generated by the superimposed-image generating function 34b. That is, when X-ray image data is chronologically acquired, the superimposed-image generating function 34b superimposes the 3D model M on the X-ray image data I12 that is a different frame from the X-ray image data I11 in which the positions of the feature points are determined by the determining function 34a.

Thus, the image processing apparatus 30 can shorten time from acquisition of X-ray image data until output. For example, the when the 3D model M is superimposed on the X-ray image data I11, the image processing apparatus 30 outputs a superimposed image of the X-ray image data I11 and the 3D model M after performing processing of acquiring the X-ray image data I11 and determining positions of feature points in the X-ray image data I11. On the other hand, when the 3D model M is superimposed on the X-ray image data I12, the image processing apparatus 30 can perform, before acquiring the X-ray image data I12, entire processing or part of the processing of determining positions of feature points in the X-ray image data I11 that is acquired prior thereto. The image processing apparatus 30 can then output a superimposed image of the X-ray image data I12 and the 3D model M in short time after acquiring the X-ray image data I12.

As another example, when the X-ray image data I11 is X-ray image data acquired from the subject P in which a stent graft is inserted, the superimposed-image generating function 34b acquires a subtraction image data I13. That is, the superimposed-image generating function 34b acquires the subtraction image data I13 between the X-ray image data I11 that is acquired from the subject P in which the stent graft is inserted and X-ray image data that is acquired before the stent graft is inserted. In this case, in the subtraction image data I13, a background component corresponding to bones, soft tissues, and the like of the subject P is removed, and only the stent graft is rendered. Moreover, when the X-ray image data I11 is X-ray image data that is acquired from the subject P in a state in which a contrast agent is injected, in the subtraction image I13, the stent graft and a blood vessel area of the subject P contrasted by the contrast agent are rendered. The subtraction image I13 is an example of the second X-ray image. Furthermore, because the subtraction image I13 is generated based on the X-ray image data I11, it is acquired later than the X-ray image data I11.

The determining function 34a determines positions of feature points of the stent graft in the X-ray image data I11. For example, the determining function 34a determines positions of the marker L11, the marker L12, and the marker L13 in the X-ray image data I11. Next, the superimposed-image generating function 34b determines, in the subtraction image data I13, positions corresponding to the positions of the feature points determined in the X-ray image data I11. For example, as the X-ray image data I11 and the subtraction image data I13 show substantially the same area in the subject P, the superimposed-image generating function 34b determines positions in the subtraction image data I13 corresponding to the positions of the marker L11, the marker L12, and the marker L13 in the X-ray image data I11, as the positions of the marker L11, the marker L12, and the marker L13 in the subtraction image data I13.

The superimposed-image generating function 34b then superimposes the 3D model M on the subtraction image data I13 at a position based on the positions of the feature points determined by the determining function 34a. For example, the superimposed-image generating function 34b superimposes the 3D model M1 on the subtraction image data I13 such that the marker L11', the marker L12', and the marker L13' in the 3D model M1 match with the positions of the marker L11, the marker L12, and the marker L13 determined in the subtraction image data I13. Thus, the superimposed-image generating function 34b generates a superimposed image I28. Moreover, the output function 34d outputs the superimposed image I28 generated by the superimposed-image generating function 34b.

Figure 10:
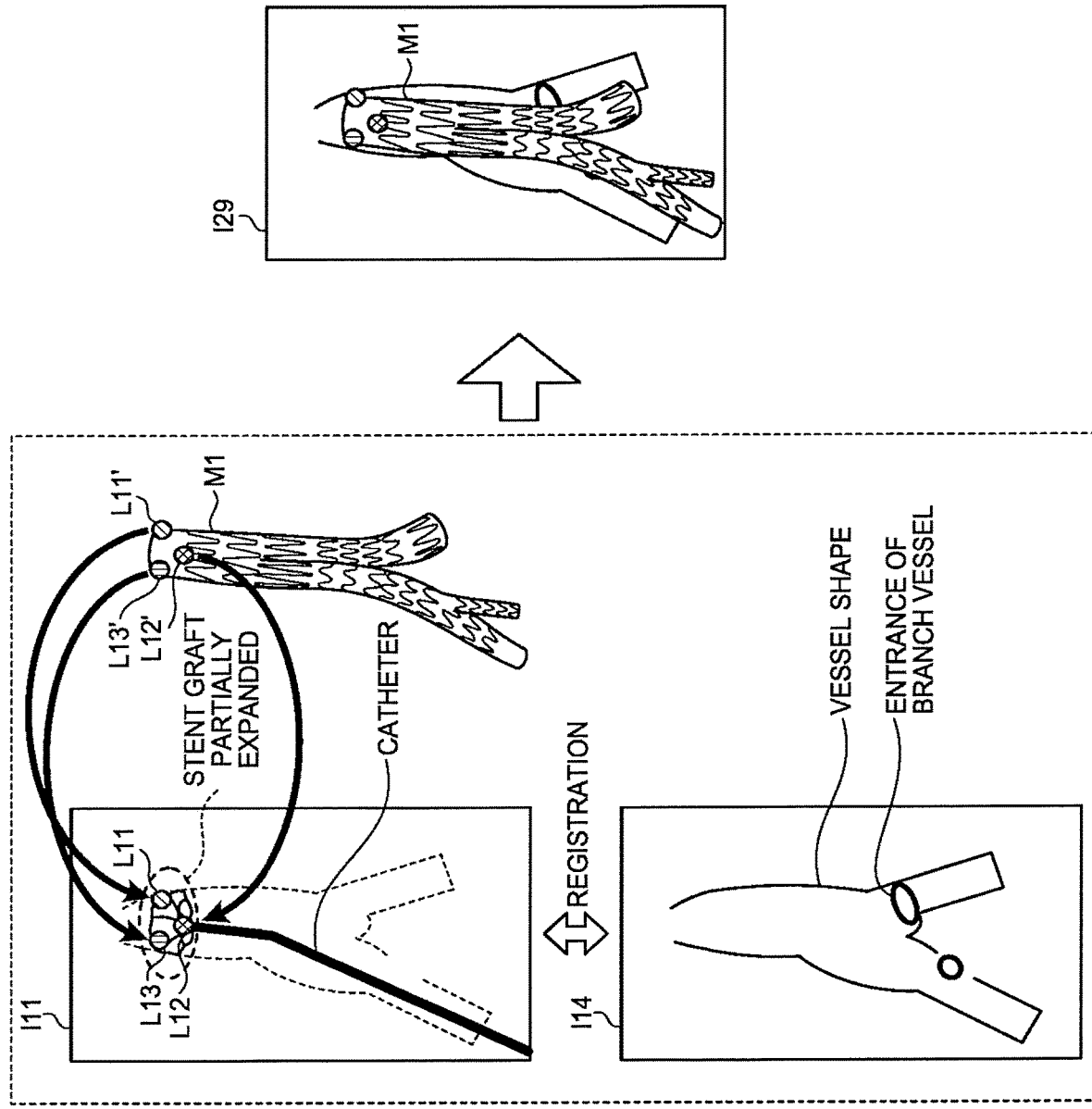
FIG. 10 is a diagram for describing generation of a superimposed image according to a third embodiment.

As another example, the superimposed-image generating function 34b acquires image data I14 that expresses a blood vessel of the subject P. For example, the superimposed-image generating function 34b acquires the image data I14 that expresses a blood vessel shape and an entrance of a branch vessel in the subject P as illustrated in FIG. 10. The image data I14 is an example of the second X-ray image. Moreover, FIG. 10 is a diagram for describing generation of a superimposed image according to the third embodiment.

For example, the superimposed-image generating function 34b first acquires X-ray image data acquired from the subject P in which a contrast agent is injected, and acquires a blood vessel shape of the subject P from the X-ray image data.

As an example, the superimposed-image generating function 34b extracts a region having a pixel value larger than a threshold from the X-ray image data that has been acquired in a state in which a positive contrast agent is injected as a blood vessel region, and acquires an outline of the extracted blood vessel region as a blood vessel shape.

Next, the superimposed-image generating function 34b determines the entrance of the branch vessel (boundary between an aorta and a branch vessel) in the acquired blood vessel shape of the subject P. For example, the superimposed-image generating function 34b determines the entrance of the branch based on the boundary between a main body and the branch (position of a hole arranged in the main body) in the stent graft. Moreover, for example, the superimposed-image generating function 34b determines the entrance of the branch vessel in the blood vessel shape by receiving a specification operation from the operator.

The superimposed-image generating function 34b then generates the image data I14 that indicates the blood vessel shape of the subject P and the entrance of the branch vessel. For example, the superimposed-image generating function 34b generates the image data I14 in which an outline of a vessel area is indicated by a curved line and an outline (rim) of the entrance of the branch vessel is indicated by an ellipse as illustrated in FIG. 10.

The determining function 34a determines positions of feature points of the stent graft in the X-ray image data I11. For example, the determining function 34a determines positions of the marker L11, the marker L12, and the marker L13 in the X-ray image data I11. Next, the superimposed-image generating function 34b determines, in the image data I14, positions corresponding to the positions of the feature points determined in the X-ray image data I11.

For example, the superimposed-image generating function 34b registers the X-ray image data I11 and the image data I14 as illustrated in FIG. 10. For example, the superimposed-image generating function 34b can register the X-ray image data I11 and the image data I14 based on the blood vessel shape and the like of the subject P in the respective image data. Thus, the superimposed-image generating function 34b determines the positions of the marker L11, the marker L12, and the marker L13 in the image data I14.

The superimposed-image generating function 34b then superimposes the 3D model M on the image data I14 at a position based on the positions of the feature points determined by the determining function 34a. For example, the superimposed-image generating function 34b superimposes the 3D model M1 on the image data I14 such that the marker L11', the marker L12', and the marker L13' in the 3D model M1 match with the positions of the marker L11, the marker L12, and the marker L13 determined in the image data I14. Thus, the superimposed-image generating function 34b generates a superimposed image I29 as illustrated in FIG. 10.

Moreover, the output function 34d outputs the superimposed image I29 generated by the superimposed-image generating function 34b. Thus, the image processing apparatus 30 makes it easy to grasp a position and an orientation of a stent graft in a subject, and can support determination of a position at which the stent graft is indwelled by presenting information relating to a vessel of the subject P including a position of an entrance of a branch vessel and the like.

The first to the third embodiments have been described so far, but there may be implementation by various different embodiments other than the first to the third embodiments.

In the embodiments described above, markers put on a stent graft have been explained as feature points of the stent graft, but embodiments are not limited thereto.

For example, the determining function 34a detects information corresponding to a shape of a stent graft in the X-ray image data I11 as a feature point. The information corresponding to a shape of a stent graft is information indicating a characteristic portion, for example, in an outline, a core line, or the like of the stent graft.

For example, the determining function 34a detects, in the X-ray image data I11, information indicating a portion at which a curvature of an outline of a stent graft is at its maximum value (a distal end of the stent graft, a bifurcating portion, or the like) as a feature point. Moreover, for example, the determining function 34a detects, in the X-ray image data I11, information indicating a portion at which a curvature of a core line of the stent graft is at its maximum value (a bent portion arranged according to a blood vessel shape of the subject P) as a feature point.

Furthermore, for example, the determining function 34a detects information corresponding to a shape of a wire frame included in the stent graft in the X-ray image data I11 as a feature point. The information corresponding to a shape of a wire frame included in the stent graft is, for example, information indicating a characteristic portion in the wire frame of the stent graft.

For example, the stent graft has a wavy wire frame as illustrated in FIG. 3. In this case, the determining function 34a detects information indicating a portion at which a wavelength, an amplitude, or the like of the wavy wire frame take a predetermined value (for example, a wavelength or an amplitude of the wire frame positioned at the distal end of the stent graft, or the like) in the X-ray image data I11 as a feature point. Moreover, for example, the determining function 34a detects information indicating a portion at which an interval between wire frames takes a predetermined value (for example, a minimum value of interval of the wire frames, or the like) in the X-ray image data I11 as a feature point.

Furthermore, in the embodiment described above, a stent graft has been explained as an example a device, but embodiments are not limited thereto. For example, the determining function 34a determines a position of a feature point of a stent other than the stent graft in the first X-ray image.

For example, a stent that is used in a technique of expanding a narrowing part of a vessel has a cylindrical wire frame, and is inserted into a body of a subject in a state of being fit outside a balloon portion of a balloon catheter. The balloon is expanded at the position the narrowing part, and the stent is thereby indwelled at the position of the narrowing part. In this case, the determining function 34a detects information corresponding to a marker put on the stent or the shape of the stent, information corresponding to a shape of a wire frame in the stent, or the like in the first X-ray image acquired about the stent inserted in the subject as a feature point.

Because a stent used in the technique of expanding a narrowing part of a blood vessel is oriented in a direction along a blood vessel in which the stent is to be positioned, it is often enough if the position can be grasped. Therefore, the determining function 34a may detect only one position of a feature point of the stent. The superimposed-image generating function 34b then superimposes the 3D model expressing the stent on the first X-ray image or the second X-ray image at a position based on the position of the determined feature point, to generate a superimposed image.

Moreover, for example, the determining function 34a determines a position of a feature point of a device inserted in a body of a subject in the first X-ray image. As an example, in the technique of expanding a narrowing part of a blood vessel, a balloon catheter and a stent in a state of being fit outside a balloon portion of the balloon catheter are inserted in a body of a subject. In this case, the determining function 34a detects a position of a feature point of at least either one out of the balloon catheter and the stent. For example, the determining function 34a detects information corresponding to a marker put on the stent or a shape of the stent, information corresponding to a shape of a wire frame in the stent, information corresponding to a marker put on a balloon on which the stent is fit or the shape of the balloon, or the like in the first X-ray image. The superimposed-image generating function 34b then superimposes the 3D model expressing the device on the first X-ray image or the second X-ray image at a position and an orientation based on the position of the determined feature point, to generate a superimposed image. The superimposed-image generating function 34b may superimpose the 3D model expressing part of the device on the first X-ray image or the second X-ray image. For example, the superimposed-image generating function 34b superimposes the 3D model expressing the stent out of the device inserted in the body of the subject on the first X-ray image or the second X-ray image, to generate a superimposed image.

Furthermore, for example, the determining function 34a determines a position of a feature point in a device other than the stent in the first X-ray image. Examples of a device other than the stent include an artificial valve that is indwelled at a position of an aortic valve in transcatheter aortic valve implantation (TAVI), a clip-shaped device that clips an end of a mitral valve in treatment of mitral valve insufficiency, and the like.

For example, an artificial valve used in TAVI has a cylindrical wire frame. The artificial valve is housed in a catheter in a compressed state. The artificial valve is then expanded out of the catheter at a position of an aortic valve, to be indwelled at the position of the aortic valve. In this case, the determining function 34a detects information corresponding to a marker put on the artificial valve or a shape of the artificial valve, information corresponding to a shape of the wire frame in the artificial valve, or the like in the first X-ray image acquired about the artificial valve inserted in the body of the subject as a feature point.

Moreover, in the embodiments described above, the case of determining a position of a feature point by detecting the feature point in the first X-ray image has been described, but embodiments are not limited thereto. For example, the determining function 34a determines a position of a feature point in the first X-ray image by receiving a specification operation from the operator. As an example, first, the determining function 34a displays the first X-ray image on the display 32. The determining function 34a then receives a specification operation to specify a position of a feature point in the X-ray image through the input interface 31 from the operator that has viewed the first X-ray image, and thereby determines the position of the feature point in the first X-ray image.

Moreover, in the embodiments described above, the case in which the first X-ray image is chronologically acquired has been described, but embodiments are not limited thereto. For example, the X-ray diagnostic apparatus 10 acquires one or more than one piece of the X-ray image, triggered by reception of an instruction to acquire an image from the operator. Next, the determining function 34a determines positions of feature points of a device in the acquired first X-ray image, and the superimposed-image generating function 34b superimposes the 3D model on the first X-ray image or the second X-ray image at a position based on the positions of the determined feature points, to generate a superimposed image. The output function 34d outputs the generated superimposed image. In this case, the operator can grasp a position of the device in the subject at the time of acquisition of the first X-ray image (at the time of instruction to acquire an image) easily.

Furthermore, in the embodiments described above, it has been described that a 3D model is enlarged or reduced such that multiple feature points determined in the first X-ray image and multiple feature points in the 3D model match with each other. In other words, it has been described that an enlargement ratio of the 3D model is determined based on an interval between the multiple feature points determined in the first X-ray image, but embodiments are not limited thereto.

For example, the superimposed-image generating function 34b first determines a position in a depth direction of the feature point determined in the first X-ray image based on three-dimensional information indicating arrangement of blood vessels of the subject P. The three-dimensional information indicating arrangement of blood vessels of the subject P is, for example, a three-dimensional blood vessel image showing blood vessels of the subject P.

As an example, the acquiring function 110a in the X-ray diagnostic apparatus 10 performs rotational shooting with respect to the subject P, and reconstructs three-dimensional blood vessel image from the acquired projection data. In this case, both the first X-ray image and the second X-ray image are acquired by the X-ray diagnostic apparatus 10, and positional relation between two is obvious. Therefore, the superimposed-image generating function 34b can use the three-dimensional blood vessel image as three-dimensional information indicating arrangement of blood vessels of the first X-ray image.

Alternatively, a medical image diagnostic apparatus other than the X-ray diagnostic apparatus may acquire a three-dimensional blood vessel image that shows blood vessels of the subject P. For example, the three-dimensional blood vessel image may be CT image data that is acquired by an X-ray CT apparatus. In this case, the superimposed-image generating function 34b determines the positional relation by performing registration between the first X-ray image and the three-dimensional blood vessel image, and can use the three-dimensional blood vessel image as three-dimensional information indicating arrangement of blood vessels of the first X-ray image.

For example, when a stent, such as a stent graft, is inserted in the body of the subject P, the stent is positioned inside either one of the blood vessels in the subject P. That is, the feature points determined in the first X-ray image are also positioned inside the blood vessel of the subject P. From the above, the superimposed-image generating function 34b can determine a position in a depth direction of a feature point determined in the first X-ray image based on the three-dimensional information indicating the arrangement of the blood vessels of the first X-ray image.

The superimposed-image generating function 34b then superimposes the 3D model at an enlargement ratio based on the determined position in a depth direction on the first X-ray image or the second X-ray image, to generate a superimposed image. Specifically, the superimposed-image generating function 34b reduces the 3D model more as the determined position is deeper inside (that is, the determined position is farther from the X-ray tube 102). Thus, the superimposed-image generating function 34b can generate a superimposed image, adjusting the size of the 3D model appropriately with respect to the first X-ray image or the second X-ray image. Moreover, when the enlargement ratio of the 3D model is determined based on an interval between feature points, the enlargement ratio of the 3D model can vary depending on whether the stent is housed inside the catheter or expanded. On the other hand, when the enlargement ratio of the 3D model is determined based on the three-dimensional information indicating arrangement of blood vessels of the subject P, the enlargement ratio of the 3D model can be determined appropriately regardless of on whether the stent is housed inside the catheter or expanded.

Note that the three-dimensional information indicating arrangement of blood vessels may include information about a heart. For example, an artificial valve used in TAVI and a clip-shaped device used in treatment of mitral valve insufficiency are positioned inside a blood vessel of the subject P or inside the heart. That is, a feature point determined in the first X-ray image is also positioned inside the blood vessel or inside the heard of the subject P. From the above, the superimposed-image generating function 34b can determine a position in a depth direction of a feature point determined in the first X-ray image based on the three-dimensional information including the information about the heart. The superimposed-image generating function 34b then superimposes the 3D model at an enlargement ratio based on the determined position in a depth direction on the first X-ray image or the second X-ray image, to generate a superimposed image.

Moreover, the superimposed-image generating function 34b may further superimpose three-dimensional information indicating arrangement of blood vessels of the subject P. For example, the superimposed-image generating function 34b generates a two-dimensional blood-vessel area image based on a three-dimensional blood vessel image acquired from the subject P, and further superimposes the generated blood-vessel area image on the first X-ray image, to generate a superimposed image.

For example, the superimposed-image generating function 34b first generates a two-dimensional blood-vessel area image based on the three-dimensional blood vessel image and an acquisition direction of the first X-ray image. As an example, the superimposed-image generating function 34b acquires information about an imaging system at the time of acquisition of the first X-ray image from the X-ray diagnostic apparatus 10, and determines a acquisition direction of the first X-ray image based on the acquired information. The information about an imaging system is, for example, information indicating a tilting or moving state of the tabletop 104, a rotating or moving state of the C-arm 105, and the like. The superimposed-image generating function 34b then generates a rendering image in which a three-dimensional blood vessel image is rendered according to the determined acquisition direction, as a blood-vessel area image. Furthermore, the superimposed-image generating function 34b superimposes the blood-vessel area image and the 3D model on the first X-ray image, to generate a superimposed image. The processing of superimposing a blood-vessel area image on an X-ray image is also referred to as three-dimensional roadmap. As a rendering method to generate a rendering image from a three-dimensional blood vessel image, volume rendering, surface rendering, ray summation, maximum intensity projection (MIP), minimum intensity projection (MinIP), and the like can be applied as appropriate.

To the blood-vessel area image, a landmark can be further added. The landmark is, for example, a symbol corresponding a characteristic portion on a device. As an example, the landmark is added to respective positions in the blood-vessel area image corresponding to a distal end portion or a branch of a stent graft that is arranged at a target position. Note that a three-dimensional roadmap using the blood-vessel area image to which the landmark is added is referred to as a landmark-added three-dimensional roadmap.

Figure 11:
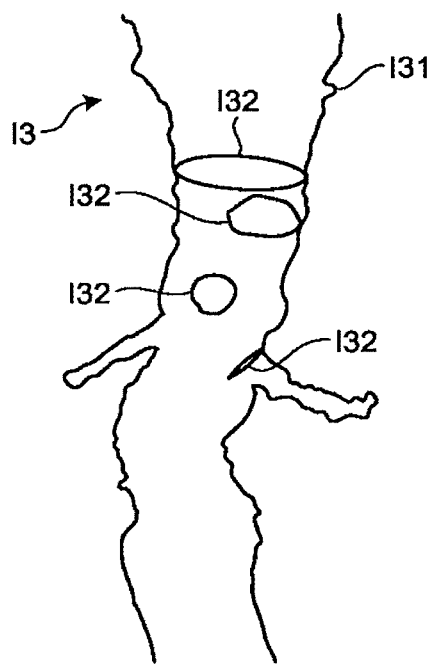
FIG. 11 is a diagram illustrating an example of a blood area image according to a fourth embodiment.

For example, the superimposed-image generating function 34b generates a blood-vessel area image I3 in which a landmark I32 is added to a blood vessel area I31 as illustrated in FIG. 11. For example, the superimposed-image generating function 34b receives an input operation from the operator through the input interface 31, and adds the landmark I32 at a position specified in the blood vessel area I31. As an example, the operator specifies, in the blood vessel area I31, a position corresponding to a distal end portion or a branch portion of a stent graft that is positioned at a target position. The superimposed-image generating function 34b adds the landmark I32 at the position specified by the operator, and thereby generates the blood-vessel area image I3. FIG. 11 is a diagram illustrating an example of a blood-vessel area image according to a fourth embodiment. The superimposed-image generating function 34b then superimposes the blood-vessel area image I3 and a 3D model expressing the stent graft on the first X-ray image, to generate a superimposed image.

For example, when the X-ray images are chronologically acquired, the superimposed-image generating function 34b sequentially generates blood-vessel area images according to an acquisition direction of the first X-ray image newly acquired. Moreover, the superimposed-image generating function 34b superimposes the newly generated blood-vessel area image and a 3D model on the first X-ray image, to generate superimposed images sequentially. The output function 34d sequentially outputs the newly generated superimposed images.

The case of superimposing a blood-vessel area image on the first X-ray image has been described as an example, but the blood-vessel area image may be superimposed on the second X-ray image. For example, when X-ray images are chronologically acquired, the superimposed-image generating function 34b sequentially generates blood-vessel area images according to an acquisition direction of the newly acquired first X-ray image. Moreover, the superimposed-image generating function 34b superimposes the newly generated blood-vessel area image and the 3D model on the second X-ray image, to generate a superimposed image. The output function 34d sequentially outputs the newly generated superimposed images.

Furthermore, in the embodiments described above, the case in which the image processing apparatus 30 includes the processing circuitry 34 having the determining function 34a, the superimposed-image generating function 34b, and the deformation processing function 34c has been described, but embodiments are not limited thereto. For example, the processing circuitry 110 in the X-ray diagnostic apparatus 10 may have functions corresponding to the determining function 34a, the superimposed-image generating function 34b, and the deformation processing function 34c.

Figure 12:
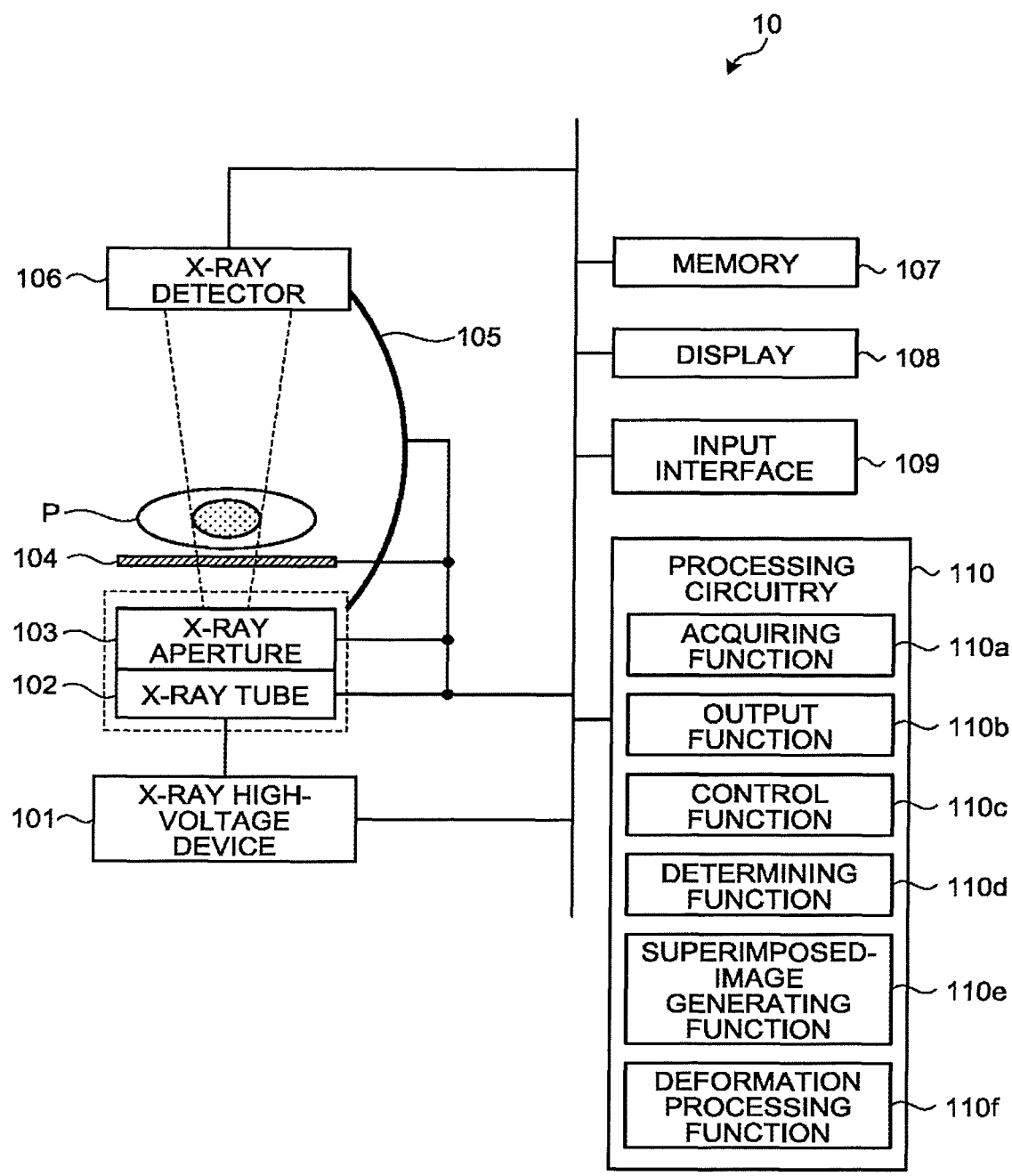
FIG. 12 is a block diagram illustrating an example of a configuration of an X-ray diagnostic apparatus according to the fourth embodiment.

For example, the processing circuitry 110 in the X-ray diagnostic apparatus 10 includes a determining function 110d, a superimposed-image generating function 110e, and a deformation processing function 110f in addition to the acquiring function 110a, the output function 110b, and the control function 110c as illustrated in FIG. 12. The determining function 110d is a function corresponding to the determining function 34a. Moreover, the superimposed-image generating function 110e is a function corresponding to the superimposed-image generating function 34b. Furthermore, the deformation processing function 110f is a function corresponding to the deformation processing function 34c. FIG. 12 is a block diagram illustrating an example of a configuration of the X-ray diagnostic apparatus 10 according to the fourth embodiment.

In the case illustrated in FIG. 12, the acquiring function 110a acquires the first X-ray image from the subject P in which a device is inserted. Moreover, the determining function 110d determines a position of a feature point in the first X-ray image acquired by the acquiring function 110a. The deformation processing function 110f may deform a 3D model expressing the device based on the first X-ray image. Moreover, the superimposed-image generating function 110e superimposes the 3D model on the first X-ray image or the second X-ray image at a position based on the position of the feature point determined by the determining function 110d, to generate a superimposed image. The output function 110b outputs the superimposed image. For example, the output function 110b displays the superimposed image on the display 108, or outputs to the image storage apparatus 20 or the image processing apparatus 30.

The respective components of the respective devices according to the embodiments described above are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Furthermore, the image processing method described in the above embodiments can be implemented by executing a program that has been prepared in advance by a computer such as a personal computer and a workstation. This program can be distributed through a network such as the Internet. Furthermore, this program can be stored in a computer-readable non-transitory recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments described above, a position of a device inside a subject can be grasped easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a memory configured to store a 3D model expressing a device, wherein the 3D model includes information indicating a position of a marker put on the device; and
processing circuitry configured to
determine a position of a feature point of the device in a first X-ray image that is acquired from one direction;
generate a superimposed image in which the 3D model is superimposed on any one of the first X-ray image and a second X-ray image that is acquired later than the first X-ray image such that the position of the marker included in the 3D model matches with the position of the feature point determined in the first X-ray image, wherein the 3D model is 3D data used when manufacturing the device or other 3D data acquired by performing modeling by imaging the device from multiple angles; and
superimpose the 3D model on any one of the first X-ray image and the second X-ray image at a position based on the determined position of the feature point,
wherein the processing circuitry is further configured to detect the feature point in the first X-ray image, thereby determining the position of the feature point, and detect information corresponding to a shape of a wire frame of the device in the first X-ray image as the feature point.

2. The image processing apparatus according to claim 1, wherein
the processing circuitry is configured to determine position of a plurality of the feature points in the first X-ray image, and superimpose the 3D model at a position and an orientation based on the determined positions of the feature points.

3. The image processing apparatus according to claim 2, wherein
the processing circuitry is configured to determine positions of three or more of the feature points in the first X-ray image.

4. The image processing apparatus according to claim 1, wherein
the processing circuitry is configured to detect the feature point in the first X-ray image, thereby determining the position of the feature point.

5. The image processing apparatus according to claim 4, wherein
the processing circuitry is configured to detect a marker put on the device in the first X-ray image as the feature point.

6. The image processing apparatus according to claim 5, wherein
the processing circuitry is configured to detect a marker put on at a distal end of the device in the first X-ray image as the feature point.

7. The image processing apparatus according to claim 6, wherein
the processing circuitry is further configured to detect a marker that is put on at a middle portion of the device in the first X-ray image as the feature point.

8. The image processing apparatus according to claim 6, wherein
the device is a stent graft that has at least one of a branch, and
the processing circuitry is further configured to detect a marker put on the branch in the first X-ray image as the feature point.

9. The image processing apparatus according to claim 4, wherein
the processing circuitry is configured to detect information corresponding to a shape of the device in the first X-ray image as the feature point.

10. The image processing apparatus according to claim 4, wherein
the processing circuitry is configured to detect information corresponding to a shape of a wire frame of the device in the first X-ray image as the feature point.

11. The image processing apparatus according to claim 1, wherein
the processing circuitry is further configured to deform the 3D model based on the first X-ray image, and superimpose the 3D model subjected to deformation on any one of the first X-ray image and the second X-ray image.

12. The image processing apparatus according to claim 11, wherein
the device is a stent that is inserted into a blood vessel of a subject in a state of being housed in a catheter, and
the processing circuitry is configured to acquire an expansion state of the stent out of the catheter based on the first X-ray image, and deform the 3D model according to the expansion state.

13. The image processing apparatus according to claim 11, wherein
the processing circuitry is configured to acquire a blood vessel shape of a subject in which the device is inserted based on the first X-ray image, and deform the 3D model according to the blood vessel shape.

14. The image processing apparatus according to claim 1, wherein
the processing circuitry is configured to generate a superimposed image in which the 3D model expressing a shape of the device on any one of the first X-ray image and the second X-ray image.

15. The image processing apparatus according to claim 1, wherein
the device is a stent graft that has at least one branch, and
the processing circuitry is configured to generate a superimposed image in which the 3D model indicating a position and an orientation of the branch of the stent graft is superimposed on any one of the first X-ray image and the second X-ray image.

16. The image processing apparatus according to claim 1, wherein
the processing circuitry is configured to determine a position in depth direction of the feature point based on three-dimensional information that indicates arrangement of blood vessels of a subject, and superimpose the 3D model at an enlargement ratio based on the determined position in depth direction.

17. The image processing apparatus according to claim 1, wherein the 3D model is 3D data used when manufacturing the device.

18. An X-ray diagnostic apparatus comprising:
a memory configured to store a 3D model expressing a device, wherein the 3D model includes information indicating a position of a marker put on the device; and
processing circuitry configured to:
acquire a first X-ray image;
determine a position of a feature point of the device in the first X-ray image that is acquired from one direction;
generate a superimposed image in which the 3D model expressing the device is superimposed on any one of the first X-ray image and a second X-ray image that is different from the first X-ray image such that the position of the marker included in the 3D model matches with the position of the feature point determined in the first X-ray image, wherein the 3D model is 3D data used when manufacturing the device or other 3D data acquired by performing modeling by imaging the device from multiple angles; and superimpose the 3D model on any one of the first X-ray image and the second X-ray image at a position based on the determined position of the feature point, wherein the processing circuitry is further configured to detect the feature point in the first X-ray image, thereby determining the position of the feature point, and detect information corresponding to a shape of a wire frame of the device in the first X-ray image as the feature point.

19. An image processing method comprising:

storing a 3D model expressing a device in a memory, wherein the 3D model includes information indicating a position of a marker put on the device;

determining a position of a feature point of the device in a first X-ray image that is acquired from one direction; and generating a superimposed image in which the 3D model is superimposed on any one of the first X-ray image and a second X-ray image that is acquired later than the first X-ray image at a position based on the feature point such that the position of the marker included in the 3D model matches with the position of the feature point determined in the first X-ray image, wherein the 3D model is 3D data used when manufacturing the device or other 3D data acquired by performing modeling by imaging the device from multiple angles, wherein the method further comprises detecting the feature point in the first X-ray image, thereby determining the position of the feature point, and detecting information corresponding to a shape of a wire frame of the device in the first X-ray image as the feature point.

* * * * *